US006039970A

United States Patent [19]
Callegaro et al.

[11] Patent Number: 6,039,970
[45] Date of Patent: Mar. 21, 2000

[54] PROCESS FOR THE PREPARATION OF MICROSPHERES CONTAINING BIOLOGICALLY ACTIVE COMPONENTS

[75] Inventors: Lanfranco Callegaro, Padua; Aurelio Romeo, Rome; Luca Benedetti, Vicenza, all of Italy

[73] Assignee: Fidia S.p.A., Abano Terme, Italy

[21] Appl. No.: 09/231,353

[22] Filed: Jan. 13, 1999

Related U.S. Application Data

[62] Division of application No. 08/169,558, Dec. 20, 1993, which is a continuation of application No. 07/890,108, May 29, 1992, abandoned.

[30] Foreign Application Priority Data

May 31, 1991 [IT] Italy ............................... PD91A0102

[51] Int. Cl.[7] ............................................ A61K 9/16
[52] U.S. Cl. ..................... 424/434; 424/489; 424/499; 514/54; 514/866
[58] Field of Search ....................... 424/434, 489, 424/499; 514/54, 866

[56] References Cited

U.S. PATENT DOCUMENTS

| | | |
|---|---|---|
| 4,462,983 | 7/1984 | Azria et al. . |
| 4,847,091 | 7/1989 | Illum . |
| 4,853,226 | 8/1989 | Machida et al. . |
| 4,904,479 | 2/1990 | Illum . |
| 4,925,673 | 5/1990 | Steiner . |
| 4,946,870 | 8/1990 | Partain, III et al. . |
| 4,965,353 | 10/1990 | della Valle et al. . |
| 5,008,116 | 4/1991 | Cahn . |
| 5,073,543 | 12/1991 | Marshall et al. . |
| 5,108,759 | 4/1992 | Ranney . |
| 5,204,108 | 4/1993 | Illum . |
| 5,629,011 | 5/1997 | Illum ........................................ 424/434 |
| 5,707,644 | 1/1998 | Illum ........................................ 424/434 |
| 5,804,212 | 9/1998 | Illum ........................................ 424/434 |
| 5,833,891 | 11/1998 | Subramaniam et al. .................... 264/7 |
| 5,856,299 | 1/1999 | Righetto et al. ............................ 514/8 |
| 5,874,029 | 2/1999 | Subramaniam et al. ................... 264/12 |
| 5,879,359 | 3/1999 | Dorigatti et al. ......................... 606/152 |
| 5,939,323 | 8/1999 | Valentini et al. ........................ 435/395 |

FOREIGN PATENT DOCUMENTS

| | | |
|---|---|---|
| 47099 | 6/1990 | Australia . |
| A1 0122036 | 10/1984 | European Pat. Off. . |
| 0251905 | 1/1988 | European Pat. Off. . |
| WO 8703197 | 6/1987 | WIPO . |
| WO 8809163 | 12/1988 | WIPO . |
| WO 8903207 | 4/1989 | WIPO . |
| WO 9106282 | 5/1991 | WIPO . |

OTHER PUBLICATIONS

Greissman et al, Intensive Care Med 22:495–499 (1996).
Illum, "Microspheres As a Potential Controlled Release Nasal Drug Delivery System," pp. 205–210.
Fisher et al., J. Pharm. Pharmacol. 37:38–41 (1985).
Sugibayashi et al., Biomaterials 1982, vol. 3, pp. 181–186 (Jul.).
Ratcliffe et al., J. Pharm. Pharmacol. 36:431–436 (1984).
Alphabetical List of Compounds.
Davis et al., "Microspheres as Controlled–Release Systems for Parenteral and Nasal Administration", pp. 201–213.
Illum et al., International Journal of Pharmaceutics, 46:261–265 (1988).

(List continued on next page.)

Primary Examiner—Robert H. Harrison
Attorney, Agent, or Firm—Birch, Stewart, Kolasch & Birch, LLP

[57] ABSTRACT

The present invention is directed to a microsphere for the controlled release of a biologically active molecule which comprises a biologically active molecule and an ester of hyaluronic acid or mixtures of said esters of hyaluronic acids, and wherein said biologically active molecule is surrounded by or adhered to said ester of hyaluronic acid, and wherein said microsphere has a diameter of between 1 $\mu$m to 100 $\mu$m.

6 Claims, 8 Drawing Sheets

OTHER PUBLICATIONS

Bodmeier et al., Pharmaceutical Research, vol. 6, No. 5, 1989.

Hermens et al., Pharmaceutical Research, vol. 7, No. 2, 1990.

Illum et al., International Journal of Pharmaceutics, 39:189–199 (1987).

M. Bendetti et al., Journal of Controlled Release, 13:33–41 (1990).

Langer, Science, 249:1527–1533 (1990).

PROCESS FOR THE PREPARATION OF MICROSPHERES CONTAINING BIOLOGICALLY ACTIVE COMPONENTS

This application is a divisional of Ser. No. 08/169,558 filed on Dec. 20, 1993, which is a continuation of Ser. No. 07/890,108 filed on May 29, 1992, abandoned.

FIELD OF THE INVENTION

An object of the, invention is a composition of microspheres and a process for their preparation starting with biodegradable and bioabsorbable semisynthetic polymers and single molecules or mixtures of the same having pharmacological activity, allowing the chemical characteristics of the semisynthetic polymer used and the biological or pharmacological activity of the molecules to remain unaltered, guaranteeing controlled release depending on the hydrophilic properties of the chemical substituents present on the semisynthetic polymer.

DESCRIPTION OF RELATED ART

Proteins and peptides are today considered to be an important base for therapeutic agents. Recombinant DNA technology has made it possibile to produce many such macromolecular agents with interesting and useful biological and pharmacological properties. The enormous technological advancement in chemical synthesis has made many polypeptides with high pharmacological activity accessible. For these drugs however problems still persist regarding stability and their administration to man. When an active principle is administered to man, it is essential to guarantee that its pharmacological activity will remain unaltered and that its release will be controlled, in order to avoid undesirable side-effects. It is known that these macromolecular agents are not usually efficacious after oral administration, since they are rapidly degraded and deactivated by the proteolytic enzymes present in the gastrointestinal tract.

Even when these macromolecules do resist enzymatic digestion, their absorption is often very slight because of their large size. Other routes of administration, such as by nose, mouth, vagina, rectum and through the skin, have been used for the absorption of proteins and peptides but bioavailability proved to be low and variable on account of the intrinsic characteristics of the active principle. Consequently, these molecules are normally administered by the parenteral route, even though this route, too, has its disadvantages, which are mainly linked to rapid elimination from the bloodstream. Over the past decade remarkable progress has been made in pharmaceutical technology dedicated to the preparation of formulations which allow, on the one hand, for the intrinsic activity of proteins to be preserved and, on the other, for their controlled release (Langer R., Science 1527, 1990).

The use of synthetic or partially natural polymeric matrixes means that drug release is now reproducible, guaranteeing constant concentrations in the bloodstream, thereby avoiding repeated administrations with the consequent risk of side effects.

However, the use of these polymeric matrices has given rise to a series of new problems linked essentially to the very nature of the polymers used, such as their toxicity and the toxicity of their degradation products, biocompatibility, and the removal of deposits of undegradable debris.

Current research is aimed at identifying and developing bioabsorbable and biodegradable polymers, partly or wholly made of natural substances, capable of the controlled release of biologically and pharmacologically active molecules, which are able to protect these molecules from degradation while allowing for their prolonged release, and without affinity for fibrous organic tissues which might alter their release properties, they should not present undesirable reactivity towards pharmacologically active molecules, and neither they, nor their degradation products should be immunogenic.

Examples of natural polymers widely used as release systems for pharmacologically active molecules such as hyaluronic acid have been described in U.S. Pat. No. 4,851,521 and U.S. Pat. No. 4,965,353; alginic acid in EP Publ. No. 0251905; chitosan in EP Publ. No. 0341745; and gellan of the acidic polysaccharides.

Hyaluronic acid is a polysaccharide widely distributed in animal organisms, and is composed of alternating units of D-glucuronic acid and N-acetyl-D-glucosamine. The mean molecular weight varies between $2 \times 10^4$ and $7 \times 10^6$ according to the purification method used. Hyaluronic acid has been used, as described, for example, in U.S. Pat. No. 4,772,419, to prevent adhesion and tissue enlargement. U.S. Pat. No. 4,636,524 also describes a release system for biologically active substances to be dispersed in the molecular "cage" formed by the meshwork of hyaluronic acid gel. Hyaluronic acid has also been described in the literature as a carrier for drugs trapped in the biodegradable, collagen-based matrix. In U.S. Pat. Nos. 4,851,521 and 4,965,353, a chemical method is reported for the esterification of carboxy groups of hyaluronic acid with therapeutically active or inactive alcohols (HYAFF). With this chemical modification, the chemico-physical properties of the polymer change too, such as the hydrophobic and hydrophilic properties of the polymer, while its chemical structure of the polysaccharide remains unaltered, as set forth below.

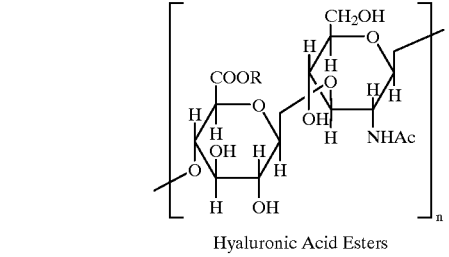

Hyaluronic Acid Esters

Moreover, various methods for the preparation of systems for the controlled release of biologically active substances are described in the literature.

For instance microspheres containing biologically and/or pharmacologically active molecules are described in the PCT patent WO 89/03207. These release systems include the association of pharmacologically and/or biologically active molecules, denaturable like polypeptides, with natural polymers (starch, gelatin or albumin). The use of hyaluronic and and/or its derivatives as a polymeric carrier to prepare formulations (microspheres) to be used for the release of active substances through the mucosa, such as the vaginal or nasal mucosa, is not described.

The in vitro characterization of the release of pharmacologically active substances, not of a proteic or glycosphingolipid nature, from microspheres prepared with hyaluronic acid esters is described in the paper "Microspheres of Hyaluronic Acid Esters Fabrication Methods and in vivo Hydrocortisone Release" by Benedetti et al., Journal of Controlled Release 13, 33–41 (1990).

Of the various technologies developed for the manufacture of microspheres, the most successful have been the "evaporation" and "extraction" techniques. Both of these processes require the preparation of an emulsion of two unmixable liquids. The emulsifying phase, known as the discontinuous phase, is constituted by microdroplets of a solvent containing modified hyaluronic acid and the substance, or suitable mixtures of biologically and/or pharmacologically active substances. The other phase of the emulsion, known as the continuous phase, is represented by a second solvent in which the microdroplets are homogeneously dispersed. When the emulsion is stable, the discontinuous phase is removed either by evaporation or extraction according to the type of technique employed. It is possible to obtain release systems with different characteristics according to how the biologically active substance or mixture of substances are incorporated in the microspheres. For example, when the active principle is physically dispersed in the polymer matrix constituting the microspheres, its release is controlled by the diffusion rate of the biologically and/or pharmacologically active substance through the polymer network.

The paper by Benedetti et al. (1990) refers, in particular, to the possibility of obtaining microspheres by evaporation, because the extraction method produces microspheres with very porous surfaces; and, consequently, the polymeric matrix of which they are constituted has no control over the release of the active principle (corticosteroid). The present invention, surprisingly, provides the possibility of producing, by extraction, smooth-surfaced microspheres which therefore have more control over the release of the substances which are incorporated therein.

Another advantage of the extraction technique of the present invention lies in the possibility of obtaining microspheres with a notably smaller diameter than those cited in Benedetti et al.

It therefore follows that the use of said microspheres, unlike those with a larger diameter, guarantees a greater total surface area and therefore more contact with the tissues to be treated.

The present invention describes the preparation of microspheres containing molecules of a proteic nature (such as calcitonin, insulin, immunoglobin, trophic factors such as hCNTF/hNGF) and/or of a glycosphingolipid nature (natural gangliosides or their chemical derivatives), that is, the preparation of compounds which are quite different in structure, chemical-physical characteristics and stability from the compound (corticosteroid) discussed in the paper by Benedetti et al. It has been demonstrated, surprisingly, that by using this release system, the proteins associated with the polymer do not undergo degradation and maintain their biological activity.

The present invention also demonstrates the incorporation of high-molecular-weight molecules, i.e., the molecular weight of the incorporated molecules is considerably higher than that of the corticosteroid.

The possibility of preparing microspheres from HYAFF derivatives with distinct chemical-physical (hydrophilic/hydrophobic) characteristics, chosen according to the chemical-physical characteristics of the biologically active molecule used, and where the biologically active molecule is to be applied, the release time and consequent action of the pharmacologically active molecule, is described according to the present invention. As a result of the present invention, it is possible to prepare microspheres from suitable mixtures of HYAFF polymer and pharmacologically and biologically active substances, specifically designed according to the type of administration, the type of active substance and the desired action of time. It is also possible to prepare microspheres where the pharmacologically and/or biologically active substance or mixture of substances is superficially adsorbed. The principles described above for microspheres and the possibility of a pharmacological interaction aimed at the site of action are valid in this case too.

SUMMARY OF THE INVENTION

Accordingly, to the present invention is directed to a process of obtaining compositions of microspheres starting from chemically modified hyaluronic acid, having different molecular weights, and from solutions of single agents and suitable mixtures thereof, which exercise a biological and/or pharmacological action, and which can be prepared according to the desired site of their desired time of release, the type of biologically and/or pharmacologically active agent to be released, while leaving intact, the biological and pharmacological properties of the agents.

DETAILED DESCRIPTION OF THE PREFERRED EMBODIMENTS

Figure 1:
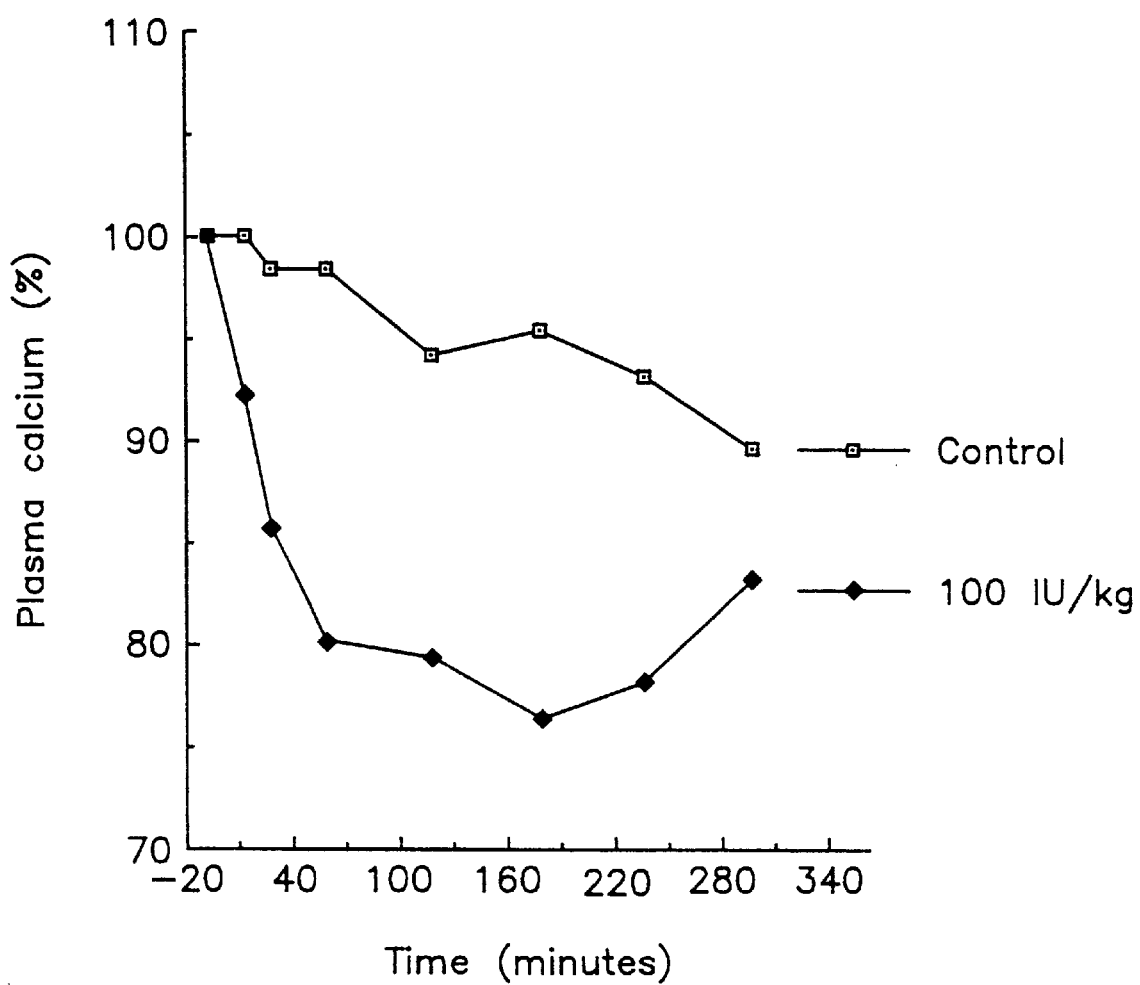
FIG. 1 shows the levels of calcium in plasma (%) after vaginal administration of calcitonin in solution.

The microspheres according to the present invention must have a particle size of between 1 and 100 μm, preferably between 1 and 15 μm, and they must have smooth surfaces. The following examples are purely illustrative of how to obtain the microspheres according to the present invention and their use and shall not be construed as limiting the scope of the invention. The molecular weight of the hyaluronic acid ester derivatives (HYAFF) which makes up the microspheres of the present invention can be, for example, in the range of about 100,000–2,000,000 Daltons, with a preferred range being between about 100,000–200,000 Daltons or between about 500,000–700,000 Daltons.

EXAMPLE 1

A hyaluronic acid ester where all the carboxy groups of hyaluronic acid are esterified with benzyl alcohol (HYAFF-11, as described in the U.S. Pat. No. 4,965,353) is dissolved in an aprotic solvent such as dimethylsulfoxide, at a concentration varying between 5 and 10% weight/volume, generally 7% w/v. Once the polymer has solubilized, a polypeptide such as human insulin, at a predetermined concentration, for example 5 I.U. per mg of polymer, is added to the solution. The mixture obtained will be referred to hereinafter as the discontinuous phase. At the same time, a mixture is prepared in a suitable reactor of high-viscosity mineral oil containing Arlacel$^R$, a non-ionic surface-active agent, at a concentration of 1% w/v.

This mixture will be referred to hereinafter as the continuous phase.

The continuous phase is kept at 25° C. while being stirred at a fixed speed of 1000 RPM, then the discontinuous phase, prepared as previously described, is added to it. In these conditions, emulsification of the two phases is instantaneous. The ratio between the two phases (discontinuous and continuous) is about 1 to 16.

After 15 minutes of stirring, acetylacetate is added.

This solvent mixes perfectly with the two phases of the emulsion but it is a nonsolvent for the polymer and the human insulin polypeptide. It has been proven that the volume of extracting solvent needed to obtain complete extraction is two and a half times the total volume of the emulsion. To facilitate extraction the stirring speed is set at 1400–1500 RPM for 10 minutes and then lowered to 500 RPM. The suspension thus obtained continues to be stirred while being pumped with a screw pump through a filter press set at 1 atmosphere. Once this filtration is complete, it is pumped through a filter of normal-hexane, this being a solvent with the double action of "drying" the preparation and solubilizing any residue surfactant which may be present on the surface of the microspheres. The product is then put in suitable containers and stored at 4° C.

In these working conditions the resulting mean particle size is 10 μm.

The quantity of incorporated insulin is 4 IU per mg of microspheres.

EXAMPLE 2

A hyaluronic acid ester wherein all the carboxy groups of hyaluronic acid are esterified with benzyl alcohol (HYAFF-11, as described in the U.S. Pat. No. 4,965,353), is dissolved in an aprotic solvent such as dimethylsulfoxide at a concentration varying from 5 to 10% weight/volume, generally 7% p/v. The solution obtained will be referred to hereinafter as the discontinuous phase. At the same time, a mixture is prepared in a suitable reactor of high-viscosity mineral oil containing Arlacel$^R$, a non-ionic surface-active agent, at a concentration of 1% p/v.

This mixture will be referred to hereinafter as the continuous phase. The continuous phase is kept at a temperature of 25° C. and stirred at a rate of 1000 RPM, while the discontinuous phase, prepared as previously described, is added to it.

In these conditions, emulsification of the two phases is instantaneous. The ratio between the two phases (discontinuous and continuous) is about 1 to 16.

After stirring for 15 minutes, ethyl acetate is added.

This solvent can be mixed perfectly with the two emulsion phases, but it is not a solvent for the polymer. It has been proven that the volume of extracting solvent needed to obtain complete extraction is two and a half times the total volume of the emulsion. To facilitate extraction, the stirring speed is set at 1400–1500 RPM for 10 minutes, then lowered to 500 RPM. The suspension thus obtained continues to be stirred, while being pumped by a screw pump through a filter press set at 1 atmosphere. Once this filtration is complete, it is pumped through a filter of normal-hexane, this being a solvent with the double action of "drying" the preparation and solubilizing any residue surfactant which may be present on the surface of the microspheres. The product is then put in suitable containers and stored at 4° C. The microspheres thus prepared are suspended in a phosphate buffer solution (0.01M) (ionic strength=0.15M), containing a concentration of insulin such that a protein titer of 2 U.I per mg of suspended microspheres is reached. After 15 minutes stirring with a semiautomatic system the suspension is immersed in liquid nitrogen until it is completely frozen.

Once frozen, the suspension is freeze-dried for 24 hrs and the product stored at 4° C.

The mean particle size is 15 μm. The quantity of incorporated insulin is 2 IU per mg of microsferes.

EXAMPLE 3

A hyaluronic acid ester wherein 75% of the carboxy groups of hyaluronic acid are esterified with benzyl alcohol while the remaining part is salified with sodium (HYAFF-11 p75, as described in the U.S. Pat. No. 4,965,353), is dissolved in an aprotic solvent such as dimethylsulfoxide, at a concentration varying from 5 to 10% weight/volume, generally 7% w/v. Once the polymer has solubilized, a polypeptide such as human insulin, at a predetermined concentration, for example 5 I.U. per mg of polymer, is added to the solution. The mixture thus obtained will be referred to hereinafter as the discontinuous phase. At the same time a mixture is prepared in a suitable reactor of high-viscosity mineral oil containing Arlacel$^R$, a non-ionic surface-active agent, at a concentration of 1% w/v.

This mixture will be referred to hereinafter as the continuous phase. The continuous phase is kept at a temperature of 25° C. and stirred at a rate of 1000 RPM, while the discontinuous phase, prepared as previously described, is added to it.

In these conditions, emulsification of the two phases is instantaneous. The ratio between the two phases (discontinuous and continuous) is about 1 to 16.

After stirring for 15 minutes, ethyl acetate is added.

This solvent can be mixed perfectly with the two emulsion phases, but it is not a solvent for the polymer or the human insulin polypeptide. It has been proven that the volume of extracting solvent needed to obtain complete extraction is two and a half times the total volume of the emulsion. To facilitate extraction, the stirring speed is set at 1400–1500 RPM for 10 minutes, then lowered to 500 RPM. The suspension thus obtained continues to be stirred, while being pumped by a screw pump through a filter press set at 1 atmosphere. Once this filtration is complete, it is pumped through a filter of normal-hexane, this being a solvent with the double action of "drying" the preparation and solubilizing any residue surfactant which may be present on the surface of the microspheres. The product is then put in suitable containers and stored at 4° C.

The mean particle size is 20 μm.

The quantity of incorporated insulin is 4 IU per mg of microspheres.

EXAMPLE 4

A hyaluronic acid ester wherein all the carboxy groups of hyaluronic acid are esterified with ethyl alcohol (HYAFF-7, as described in the U.S. Pat. No. 4,965,353), is dissolved in an aprotic solvent such as dimethylsulfoxide, at a concentration varying from 5 to 10% weight/volume, generally 7% w/v. Once the polymer has solubilized, a polypeptide, such as human insulin, at a predetermined concentration, for example 5 I.U. per mg of polymer, is added to the solution. The mixture thus obtained will be referred to hereinafter as the discontinuous phase. At the same time a mixture is prepared in a suitable reactor of high-viscosity mineral oil containing Arlacel$^R$, a non-ionic surface-active agent, at a concentration of 1% w/v.

This mixture will be referred to hereinafter as the continuous phase. The continuous phase is kept at temperature of 25° C. and stirred at a rate of 1000 RPM, while the discontinuous phase, prepared as previously described, is added to it.

In these conditions, emulsification of the two phases is instantaneous. The ratio between the two phases (discontinuous and continuous) is about 1 to 16.

After stirring for 15 minutes, ethyl acetate is added.

This solvent can be mixed perfectly with the two emulsion phases, but it is not a solvent for the polymer or the human insulin polypeptide. It has been proven that the volume of extracting solvent needed to obtain complete extraction is two and a half times the total volume of the emulsion. To facilitate extraction, the stirring speed is set at 1400–1500 RPM for 10 minutes, then lowered to 500 RPM. The suspension thus obtained is stirred while being pumped by a screw pump, through a filter press set at 1 atmosphere. Once this filtration is complete, it is pumped through a filter of normal-hexane, this being a solvent with the double action of "drying" the preparation and solubilizing any residue surfactant which may be present on the surface of the microspheres. The product is then put in suitable containers and stored at 4° C.

The dimensions of the microshperes and the mean particle size is 30 μm.

The quantity of incorporated insulin is 4 I.U. per mg of microspheres.

EXAMPLE 5

A hyaluronic acid ester wherein all the carboxy groups of hyaluronic acid are esterified with ethyl alcohol (HYAFF-7, as described in the U.S. Pat. No. 4,965,353) is dissolved in an aprotic solvent such as dimethylsulfoxide, at a concentration varying from 5 to 10% weight/volume, generally 7% w/v. The solution obtained will be referred to hereinafter as the discontinuous phase. At the same time a mixture is prepared in a suitable container of high-viscosity mineral oil containing Arlacel$^R$, a non-ionic surface-active agent, at a concentration of 1% w/v.

This mixture will be referred to hereinafter as the continuous phase. It is kept at temperature of 25° C. and stirred at a rate of 1000 RPM, while the discontinuous phase, prepared as previously described, is added to it.

In these conditions, emulsification of the two phases is instantaneous. The ratio between the two phases (discontinuous and continuous) is about 1 to 16.

After stirring for 15 minutes, ethyl acetate is added.

This solvent can be mixed perfectly with the two emulsion phases, but it is not a solvent for the polymer. It has been proven that the volume of extracting solvent needed to obtain complete extraction is two and a half times the total volume of the emulsion. To facilitate extraction, the stirring speed is set at 1400–1500 for 10 minutes, then lowered to 500 RPM. The suspension thus obtained continues to be stirred, while being pumped by a screw pump through a filter press set at 1 atmosphere. Once filtration is complete, it is pumped through a normal-hexane filter, this being a solvent with the double action of "drying" the preparation and solubilizing any residue surfactant which may be present on the surface of the microspheres. The product is then put in suitable containers and stored at 4° C.

The microspheres thus prepared are suspended in a phosphate buffer solution (0.01M) (ionic strength=0.15M), containing a concentration of insulin such that a protein titer of 2 I.U. per mg of suspended microspheres is reached. After 15 minutes of stirring with a semiautomatic system the container is immersed in liquid nitrogen until the suspension has completely frozen.

Once frozen, the suspension is freeze-dried for 24 hrs and the product stored at 4° C.

The mean particle size is 30 μm.

The quantity of incorporated insulin is 2 I.U. per mg of microspheres.

EXAMPLE 6

A hyaluronic acid ester wherein all the carboxy groups of hyaluronic acid are esterified with benzyl alcohol (HYAFF-11, as described in the U.S. Pat. No. 4,965,353), is dissolved in an aprotic solvent such as dimethylsulfoxide at a concentration varying from 5 to 10% weight/volume, generally 7% w/v. Once the polymer has solubilized, a polypeptide, for example Nerve Growth Factor (NGF), at a predetermined concentration, for example 0.01% of the weight of the polymer mass, is added to the solution. The mixture thus obtained will be referred to hereinafter as the discontinuous phase. At the same time a mixture is prepared in a suitable reactor of high-viscosity mineral oil containing Arlacel$^R$, a non-ionic surface-active agent, at a concentration of 1% w/v.

This mixture will be referred to hereinafter as the continuous phase. It is kept at temperature of 25° C. and stirred at a rate of 1000 RPM, while the discontinuous phase, prepared as previously described, is added to it. In these conditions, emulsification of the two phases is instantaneous. The ratio between the two phases (discontinuous and continuous) is about 1 to 16.

After stirring for 15 minutes, ethyl acetate is added.

This solvent can be mixed perfectly with the two emulsion phases, but it is not a solvent for the polymer or the polypeptide NGF. It has been proven that the volume of extracting solvent needed to obtain complete extraction is two and a half times the total volume of the emulsion. To facilitate extraction, the stirring speed is set at 1400–1500 RPM for 10 minutes, then lowered to 500 RPM. The suspension thus obtained continues to be stirred, while being pumped by a screw pump through a filter press set at 1 atmosphere. Once this filtration is complete, it is pumped through a filter of normal-hexane, this being a solvent with the double action of "drying" the preparation and solubilizing any residue surfactant which may be present on the surface of the microspheres. The product is then put in suitable containers and stored at 4° C.

In these working conditions the resulting mean particle size is 10 μm.

The quantity of incorporated NGF is 10 ng per mg of microspheres.

EXAMPLE 7

A hyaluronic acid ester where all the carboxy groups of hyaluronic acid are esterified with benzyl alcohol (HYAFF-11, as described in the U.S. Pat. No. 4,965,353), is dissolved in an aprotic solvent such as dimethylsulfoxide, at a concentration varying from 5 to 10% weight/volume, generally 7% w/v. Once the polymer has solubilized, a polypeptide, for example Nerve Growth Factor (NGF), at a predetermined concentration, for example 0.01% of the weight of the polymer mass, is added to the solution. The solution obtained will be referred to hereinafter as the discontinuous phase. At the same time a mixture is prepared in a suitable reactor of high-viscosity mineral oil containing Arlacel$^R$, a non-ionic surface-active agent, at a concentration of 1% w/v.

This mixture will be referred to hereinafter as the continuous phase. It is kept at a temperature of 25° C. and stirred at a rate of 1000 RPM, while the discontinuous phase, prepared as previously described, is added to it.

In these conditions, emulsification of the two phases is instantaneous. The ratio between the two phases (discontinuous and continuous) is about 1 to 16.

After stirring for 15 minutes, ethyl acetate is added.

This solvent can be mixed perfectly with the two emulsion phases but it is not a solvent for the polymer. It has been proven that the volume of extracting solvent needed to obtain complete extraction is two and a half times the total volume of the emulsion. To facilitate extraction, the stirring speed is set at 1400–1500 for 10 minutes, then lowered to 500 RPM. The suspension thus obtained continues to be stirred, while being pumped by a screw pump through a filter press set at 1 atmosphere. Once this filtration is complete, it is pumped through a filter of normal-hexane, this being a solvent with the double action of "drying" the preparation and solubilizing any residue surfactant which may be present on the surface of the microspheres. Th e product is then put in suitable containers and stored at 4° C. The microspheres thus prepared are suspended in a phosphate buffer solution (0.01M) (ionic strength=0.15M), containing a concentration of NGF such that a protein titer equal to 0.01% by weight of the suspended microspheres is reached. After 15 minutes of stirring with a semiautomatic system the container is immersed in liquid nitrogen until the suspension is completely frozen.

Once frozen, the suspension is freeze-dried for 24 hrs and the product stored at 4° C.

The mean particle size is 10 μm.

The quantity of incorporated NGF is 10 ng per mg of microspheres.

EXAMPLE 8

A hyaluronic acid ester where 75% of the carboxy groups of hyaluronic acid are esterified with benzyl alcohol while the remaining part is salified with sodium (HYAFF-11 p75, as described in the U.S. Pat. No. 4,965,353), is dissolved in an aprotic solvent such as dimethylsulfoxide, at a concentration varying from 5 to 10% weight/volume, generally 7% w/v. once the polymer has solubilized, a polypeptide, for example NGF, at a predetermined concentration, for example 0.01% of the weight of the polymer mass, is added to the solution. The mixture thus obtained will be referred to hereinafter as the discontinuous phase. At the same time a mixture is prepared in a suitable reactor of high-viscosity mineral oil containing Arlacel$^R$, a non-ionic surface-active agent, at a concentration of 1% w/v.

This mixture will be referred to hereinafter as the continuous phase. It is kept at a temperature of 25° C. and stirred at a rate of 1000 RPM, while the discontinuous phase, prepared as previously described, is added to it.

In these conditions, emulsification of the two phases is instantaneous. The ratio between the two phases (discontinuous and continuous) is about 1 to 16.

After stirring for 15 minutes, ethyl acetate is added.

This solvent can be mixed perfectly with the two emulsion phases, but it is not a solvent for the polymer or the NGF polypeptide. It has been proven that the volume of extracting solvent needed to obtain complete extraction is two and a half times the total volume of the emulsion. To facilitate extraction, the stirring speed is set at 1400–1500 RPM for 10 minutes, then lowered to 500 RPM. The suspension thus obtained continues to be stirred, while being pumped by a screw pump through a filter press set at 1 atmosphere. Once this filtration is complete, it is pumped through a filter of normal-hexane, this being a solvent with the double action of "drying" the preparation and solubilizing any possible residues of surfactant which may be present on the surface of the microspheres. The product is then put in suitable containers and stored at 4° C.

The mean particle size is 15 μm.

The quantity of incorporated NGF is 10 ng per mg of microspheres.

EXAMPLE 9

A hyaluronic acid ester where all the carboxy groups of hyaluronic acid are esterified with ethyl alcohol (HYAFF-7, as described in the U.S. Pat. No. 4,965,353), is dissolved in an aprotic solvent such as dimethylsulfoxide, at a concentration varying from 5 to 10% weight/volume, generally 7% w/v. Once the polymer has solubilized, a polypeptide, for example NGF, at a predetermined concentration, for example 0.01% of the weight of the polymer mass, is added to the solution. The mixture thus obtained will be referred to hereinafter as the discontinuous phase. At the same time a mixture is prepared in a suitable reactor of high-viscosity mineral oil containing Arlacel$^R$, a non-ionic surface-active agent, at a concentration of 1% w/v.

This mixture will be referred to hereinafter as the continuous phase. It is kept at a temperature of 25° C. and stirred at a rate of 1000 RPM, while the discontinuous phase, prepared as previously described, is added to it.

In these conditions, emulsification of the two phases is instantaneous. The ratio between the two phases (discontinuous and continuous) is about 1 to 16.

After stirring for 15 minutes, ethyl acetate is added.

This solvent can be mixed perfectly with the two emulsion phases, but it is not a solvent for the polymer or for the NGF polypeptide. It has been proven that the volume of extracting solvent needed to obtain complete extraction is two and a half times the total volume of the emulsion. To facilitate extraction, the stirring speed is set at 1400–1500 RPM for 10 minutes, then lowered to 500 RPM. The suspension thus obtained continues to be stirred, while being pumped by a screw pump through a filter press set at 1 atmosphere. Once this filtration is complete, it is pumped through a filter of normal-hexane, this being a solvent with the double action of "drying" the preparation and solubilizing any residue surfactant which may be present on the surface of the microspheres. The product is then put in suitable containers and stored at 4° C.

The mean particle size is 30 μm.

The quantity of incorporated NGF is 10 ng per mg of microspheres.

EXAMPLE 10

A hyaluronic acid ester where all the carboxy groups of hyaluronic acid are esterified with ethyl alcohol (HYAFF-7, as described in the U.S. Pat. No. 4,965,353), is dissolved in an aprotic solvent such as dimethylsulfoxide, at a concentration varying from 5 to 10% weight/volume, generally 7% w/v. The solution obtained will be referred to hereinafter as the discontinuous phase. At the same time a mixture is prepared in a suitable reactor of high-viscosity mineral oil containing Arlacel$^R$, a non-ionic surface-active agent, at a concentration of 1% w/v.

This mixture will be referred to hereinafter as the continuous phase. It is kept at a temperature of 25° C. and stirred at a rate of 1000 RPM, while the discontinuous phase, prepared as previously described, is added to it. In these conditions, emulsification of the two phases is instantaneous. The ratio between the two phases (discontinuous and continuous) is about 1 to 16.

After stirring for 15 minutes, ethyl acetate is added.

This solvent can be mixed perfectly with the two emulsion phases, but it is not a solvent for the polymer. It has been proven that the volume of extracting solvent needed to obtain complete extraction is two and a half times the total volume of the emulsion. To facilitate extraction, the stirring speed is set at 1400–1500 for 10 minutes, then lowered to 500 RPM. The suspension thus obtained is stirred while being pumped by screw pump through a filter press set at 1 atmosphere. Once this filtration is complete, it is pumped through a filter of normal-hexane, this being a solvent with the double action of "drying" the preparation and solubilizing any residue surfactant which may be present on the surface of the microspheres. The product is then put in suitable containers and stored at 4° C.

The microspheres thus prepared are suspended in a phosphate buffer solution (0.01M) (ionic strength=0.15M), containing a concentration of NGF such that a protein titer equal to 0.01% in weight of the suspended microspheres is reached. After 15 minutes of stirring with a semiautomatic system the container is immersed in liquid nitrogen until the suspension is completely frozen.

Once frozen, the suspension is freeze-dried for 24 hrs and the product stored at 4° C.

The dimensions of the microspheres and the mean particle size is 30 μm.

The quantity of incorporated NGF is 10 ng per mg of microspheres.

EXAMPLE 11

A hyaluronic acid ester where all the carboxy groups of hyaluronic acid are esterified with benzyl alcohol (HYAFF-11, as described in the U.S. Pat. No. 4,965,353), is dissolved in an aprotic solvent such as dimethylsulfoxide, at a concentration varying from 5 to 10% weight/volume, generally 7% w/v. Once the polymer has solubilized, a polypeptide, for example CNTF (Ciliary Neuronotrofic Factor), at a predetermined concentration, for example 0.01% of the weight of the polymer mass, is added to the solution.

The mixture thus obtained will be referred to hereinafter as the discontinuous phase. At the same time a mixture is prepared in a suitable reactor of high-viscosity mineral oil containing Arlacel$^R$, a non-ionic surface-active agent, at a concentration of 1% w/v.

This mixture will be referred to hereinafter as the continuous phase. It is kept at temperature of 25° C. and stirred at a rate of 1000 RPM, while the discontinuous phase, prepared as previously described, is added to it.

In these conditions, emulsification of the two phases is instantaneous. The ratio between the two phases (discontinuous and continuous) is about 1 to 16.

After stirring for 15 minutes, ethyl acetate is added.

This solvent can be mixed perfectly with the two emulsion phases, but it is not a solvent for the polymer or the polypeptide CNTF. It has been proven that the volume of extracting solvent needed to obtain complete extraction is two and a half times the total volume of the emulsion. To facilitate extraction, the stirring speed is set at 1400–1500 RPM for 10 minutes, then lowered to 500 RPM. The suspension thus obtained continues to be stirred, while being pumped by a screw pump through a filter press set at 1 atmosphere. Once this filtration is complete, it is pumped through a filter of normal-hexane, this being a solvent with the double action of "drying" the preparation and solubilizing any residue surfactant which may be present on the surface of the microspheres. The product is then put in suitable containers and stored at 4° C.

In these working conditions the resulting mean particle size is 10 μm.

The quantity of incorporated CNTF is 10 ng per mg of microspheres.

EXAMPLE 12

A hyaluronic acid ester, where all the carboxy groups of hyaluronic acid are esterified with benzyl alcohol (HYAFF-11, as described in the U.S. Pat. No. 4,965,353), is dissolved in an aprotic solvent such as dimethylsulfoxide at a concentration varying from 5 to 10% weight/volume, generally 7% w/v. The solution obtained will be referred to hereinafter as the discontinuous phase. At the same time a mixture is prepared in a suitable reactor of high-viscosity mineral oil containing Arlacel$^R$, a non-ionic surface-active agent, at a concentration of 1% w/v.

This mixture will be referred to hereinafter as the continuous phase. It is kept at a temperature of 25° C. and stirred at a rate of 1000 RPM, while the discontinuous phase, prepared as previously described, is added to it.

In these conditions, emulsification of the two phases is instantaneous. The ratio between the two phases (discontinuous and continuous) is about 1 to 16.

After stirring for 15 minutes, ethyl acetate is added.

This solvent can be mixed perfectly with the two emulsion phases, but it is not a solvent for the polymer. It has been proven that the volume of extracting solvent needed to obtain complete extraction is two and a half times the total volume of the emulsion. To facilitate extraction, the stirring speed is set at 1400–1500 for 10 minutes, then lowered to 500 RPM. The suspension thus obtained continues to be stirred, while being pumped by a screw pump through a filter press set at 1 atmosphere. Once this filtration is complete, it is pumped through a filter of normal-hexane, this being a solvent with the double action of "drying" the preparation and solubilizing any residue surfactant which may be present on the surface of the microspheres. The product is then put in suitable containers and stored at 4° C.

The microspheres thus prepared are suspended in a phosphate buffer solution (0.01M) (ionic strength=0.15M), containing a concentration of CNTF (Ciliary Neuronotrofic Factor) such that a protein titer equal to 0.01% in weight of the suspended microspheres is reached. After 15 minutes of stirring with a semiautomatic system the container is immersed in liquid nitrogen until the suspension is completely frozen.

Once frozen, the suspension is freeze-dried for 24 hrs and the product stored at 4° C.

The mean particle size is 10 μm.

The quantity of incorporated CNTF is 10 ng per mg of microspheres.

EXAMPLE 13

A hyaluronic acid ester where all the carboxy groups of hyaluronic acid are esterified with ethyl alcohol (HYAFF-7, as described in the U.S. Pat. No. 4,965,353), is dissolved in an aprotic solvent such as dimethylsulfoxide, at a concentration varying from 5 to 10% weight/volume, generally 7% w/v. Once the polymer has solubilized, a polypeptide, for example CNTF (Ciliary Neronotrophic Factor), at the predetermined concentration, for example 0.01% of the weight of the polymer mass, is added to the solution.

This mixture will be referred to hereinafter as the discontinuous phase. At the same time a mixture is prepared in a suitable reactor of high-viscosity mineral oil containing Arlacel$^R$, a non-ionic surface-active agent, at a concentration of 1% w/v.

This mixture will be referred to hereinafter as the continuous phase. It is kept at a temperature of 25° C. and stirred at a rate of 1000 RPM, while the discontinuous phase, prepared as previously described, is added to it.

In these conditions, emulsification of the two phases is instantaneous. The ratio between the two phases (discontinuous and continuous) is about 1 to 16.

After stirring for 15 minutes, ethyl acetate is added.

This solvent can be mixed perfectly with the two emulsion phases, but it is not a solvent for the polymer or the polypeptide CNTF. It has been proven that the volume of extracting solvent needed to obtain complete extraction is two and a half times the total volume of the emulsion. To facilitate extraction, the stirring speed is set at 1400–1500 RPM for 10 minutes, then lowered to 500 RPM. The suspension thus obtained continues to be stirred, while being pumped by a screw pump through a filter press set at 1 atmosphere. Once this filtration is complete, it is pumped through a filter of normal-hexane, this being a solvent with the double action of "drying" the preparation and solubilizing any residue surfactant which may be present on the surface of the microspheres. The product is then put in suitable containers and stored at 4° C.

The mean particle size is 30 μm.

The quantity of incorporated CNTF is 10 ng per mg of microspheres.

EXAMPLE 14

A hyaluronic acid ester where all the carboxy groups of hyaluronic acid are esterified with ethyl alcohol (HYAFF-7, as described in the U.S. Pat. No. 4,965,353), is dissolved in an aprotic solvent such as dimethylsulfoxide, at a concentration varying from 5 to 10% weight/volume, generally 7% w/v. The solution obtained will be referred to hereinafter as the discontinuous phase. At the same time a mixture is prepared in a suitable reactor of high-viscosity mineral oil containing Arlacel$^R$, a non-ionic surface-active agent, at a concentration of 1% w/v.

This mixture will be referred to hereinafter as the continuous phase. It is kept at a temperature of 25° C. and stirred at a rate of 1000 RPM, while the discontinuous phase, prepared as previously described, is added to it.

In these conditions, emulsification of the two phases is instantaneous. The ratio between the two phases (discontinuous and continuous) is about 1 to 16.

After stirring for 15 minutes, ethyl acetate is added.

This solvent can be mixed perfectly with the two emulsion phases, but it is not a solvent for the polymer. It has been proven that the volume of extracting solvent needed to obtain complete extraction is two and a half times the total volume of the emulsion. To facilitate extraction, the stirring speed is set at 1400–1500 for 10 minutes, then lowered to 500 RPM. The suspension thus obtained continues to be stirred, while being pumped by a screw pump through a filter press set at 1 atmosphere. Once this filtration is complete, it is pumped through a filter of normal-hexane, this being a solvent with the double action of "drying" the preparation and of solubilizing any possible residues of surfactant which may be present on the surface of the microspheres. The product is then put in suitable containers and stored at 4° C.

The microspheres thus prepared are suspended in a phosphate buffer solution (0.01M) (ionic strength=0.15M) containing a concentration of CNTF (Ciliary Neuronotrophic Factor) such that a protein titer equal to 0.01% in weight of the suspended microspheres is reached. After 15 minutes of stirring with a semiautomatic system the container is immersed in liquid nitrogen until the suspension is completely frozen.

Once frozen, the suspension is freeze-dried for 24 hrs and the product stored at 4° C.

The mean particle size is 30 μm.

The quantity of incorporated CNTF is 10 ng per mg of microspheres.

EXAMPLE 15

A hyaluronic acid ester where all the carboxy groups of hyaluronic acid are esterified with benzyl alcohol (HYAFF-11, as described in the U.S. Pat. No. 4,965,353), is dissolved in an aprotic solvent such as dimethylsulfoxide, at a concentration varying from 5 to 10% weight/volume, generally 7% w/v. Once the polymer has solubilized, a polypeptide, for example NGF at the predetermined concentration, for example 0.01% of the weight of the polymer mass, and a ganglioside mixture having as major components, GM1 21%, GD12 40%, GD1b 16% and GT1b 19% (Cronassial®) are added at a ratio of 1:1000 in terms of weight.

The mixture thus obtained will be referred to hereinafter as the discontinuous phase. At the same time a mixture is prepared in a suitable reactor of high-viscosity mineral oil containing Arlacel$^R$, a non-ionic surface-active agent, at a concentration of 1% w/v.

This mixture will be referred to hereinafter as the continuous phase. It is kept at a temperature of 25° C. and stirred at a rate of 1000 RPM, while the discontinuous phase, prepared as previously described, is added to it.

In these conditions, emulsification of the two phases is instantaneous. The ratio between the two phases (discontinuous and continuous) is about 1 to 16.

After stirring for 15 minutes, ethyl acetate is added.

This solvent can be mixed perfectly with the two emulsion phases, but it is not a solvent for the polymer or the polypeptide NGF or the GA mixture (Cronassial). It has been proven that the volume of extracting solvent needed to obtain complete extraction is two and a half times the total volume of the emulsion. To facilitate extraction, the stirring speed is set at 1400–1500 RPM for 10 minutes, then lowered to 500 RPM. The suspension thus obtained continues to be stirred, while being pumped by a screw pump through a filter press set at 1 atmosphere. Once this filtration is complete, it is pumped through a filter of normal-hexane, this being a solvent with the double action of "drying" the preparation and solubilizing any residue surfactant which may be present on the surface of the microspheres. The product is then put in suitable containers and stored at 4° C.

In these working conditions, the dimensions of the microspheres and the mean particle size is 10 μm.

The quantity of incorporated NGF and GA is 10 ng and 10 μg respectively per milligram of microspheres.

EXAMPLE 16

A hyaluronic acid ester where all the carboxy groups of hyaluronic acid are esterified with benzyl alcohol (HYAFF-11, as described in the U.S. Pat. No. 4,965,353), is dissolved in an aprotic solvent such as dimethylsulfoxide, at a concentration varying from 5 to 10% weight/volume, generally 7% w/v. Once the polymer has solubilized, a ganglioside mixture (Cronassiall) at the predetermined concentration, for example 20% of the weight of the polymer, is added to the solution. The solution obtained will be referred to hereinafter as the discontinuous phase. At the same time a mixture is prepared in a suitable reactor of high-viscosity mineral oil containing Arlacel$^R$, a non-ionic surface-active agent, at a concentration of 1% w/v.

This mixture will be referred to hereinafter as the continuous phase. It is kept at a temperature of 25° C. and stirred at a rate of 1000 RPM, while the discontinuous phase, prepared as previously described, is added to it. In these conditions, emulsification of the two phases is instantaneous. The ratio between the two phases (discontinuous and continuous) is about 1 to 16.

After stirring for 15 minutes, ethyl acetate is added.

This solvent can be mixed perfectly with the two emulsion phases, but it is not a solvent for the polymer or the ganglioside mixture. It has been proven that the volume of extracting solvent needed to obtain complete extraction is two and a half times the total volume of the emulsion. To facilitate extraction, the stirring speed is set at 1400–1500 RPM for 10 minutes, then lowered to 500 RPM. The suspension thus obtained continues to be stirred, while being pumped by a screw pump through a filter press set at 1 atmosphere. Once this filtration is complete, it is pumped through a filter of normal-hexane, this being a solvent with the double action of "drying" the preparation and solubilizing any residue surfactant which may be present on the surface of the microspheres. The product is then put in suitable containers and stored at 4° C.

The microspheres thus prepared are suspended in a phosphate buffer solution (0.01M) (ionic strength=0.15M), containing a concentration of NGF such that a protein titer equal to 0.02% in weight of the suspended microspheres is reached, and such that the weight ratio of 1:1000 (NGF:gangliosides) is maintained.

After 15 minutes of stirring with a semiautomatic system the container is immersed in liquid nitrogen until the suspension is completely frozen. Once frozen, the suspension is freeze-dried for 24 hrs and the product stored at 4° C.

The mean particle size is 10 μm.

The quantity of incorporated NGF and GA is 20 ng and 20 μg, respectively, per milligram of microspheres.

EXAMPLE 17

A hyaluronic acid ester where all the carboxy groups of hyaluronic acid are esterified with ethyl alcohol (HYAFF-7, as described in the U.S. Pat. No. 4,965,353), is dissolved in an aprotic solvent such as dimethylsulfoxide, at a concentration varying from 5 to 10% weight/volume, generally 7% w/v. Once the polymer has solubilized, a polypeptide, for example NGF at the predetermined concentration, for example 0.01% of the weight of the polymer mass, and a ganglioside mixture (Cronassial®) are added to the solution at a weight ratio of 1:1000 (NGF:Cronassial®). The mixture thus obtained will be referred to hereinafter as the discontinuous phase. At the same time a mixture is prepared in a suitable reactor of high-viscosity mineral oil containing Arlacel$^R$, a non-ionic surface-active agent, at a concentration of 1% w/v.

This mixture will be referred to hereinafter as the continuous phase. It is kept at a temperature of 25° C. and stirred at a rate of 1000 RPM, while the discontinuous phase, prepared as previously described, is added to it.

In these conditions, emulsification of the two phases is instantaneous. The ratio between the two phases (discontinuous and continuous) is about 1 to 16.

After stirring for 15 minutes, ethyl acetate is added.

This solvent can be mixed perfectly with the two emulsion phases, but it is not a solvent for the polymer, the polipeptide (NGF) or the GA mixture. It has been proven that the volume of extracting solvent needed to obtain complete extraction is two and a half times the total volume of the emulsion. To facilitate extraction, the stirring speed is set at 1400–1500 RPM for 10 minutes, then lowered to 500 RPM. The suspension thus obtained continues to be stirred, while being pumped by a screw pump through a filter press set at 1 atmosphere. Once this filtration is complete, it is pumped through a filter of normal-hexane, this being a solvent with the double action of "drying" the preparation and solubilizing any residue surfactant which may be present on the surface of the microspheres. The product is then put in suitable containers and stored at 4° C.

The dimensions of the microspheres and the mean particle size is 30 μm.

The quantities of incorporated NGF and GA are 10 ng and 10 μg respectively per milligram of microspheres.

EXAMPLE 18

A hyaluronic acid ester where all the carboxy groups of hyaluronic acid are esterified with ethyl alcohol (HYAFF-7, as described in the U.S. Pat. No. 4,965,353), is dissolved in an aprotic solvent such as dimethylsulfoxide, at a concentration varying from 5 to 10% weight/volume, generally 7% w/v. Once the polymer has solubilized, a ganglioside mixture (Cronassial®) at the predetermined concentration, for example 20% of the weight of the polymer, is added to the solution. The solution thus obtained will be referred to hereinafter as the discontinuous phase.

At the same time a mixture is prepared in a suitable reactor of high-viscosity mineral oil containing Arlacel$^R$, a non-ionic surface-active agent, at a concentration of 1% w/v.

This mixture will be referred to hereinafter as the continuous phase. It is kept at a temperature of 25° C. and stirred at a rate of 1000 RPM, while the discontinuous phase, prepared as previously described, is added to it.

In these conditions, emulsification of the two phases is instantaneous. The ratio between the two phases (discontinuous and continuous) is about 1 to 16.

After stirring for 15 minutes, ethyl acetate is added.

This solvent can be mixed perfectly with the two emulsion phases, but it is not a solvent for the polymer or the ganglioside mixture. It has been proven that the volume of extracting solvent needed to obtain complete extraction is two and a half times the total volume of the emulsion. To facilitate extraction, the stirring speed is set at 1400–1500 RPM for 10 minutes, then lowered to 500 RPM. The suspension thus obtained continues to be stirred, while being pumped by a screw pump through a filter press set at 1 atmosphere. Once this filtration is complete, it is pumped through a filter of normal-hexane, this being a solvent with the double action of "drying" the preparation and solubilizing any residue surfactant which may be present on the surface of the microspheres. The product is then put in suitable containers and stored at 4° C.

The microspheres thus prepared are suspended in a phosphate buffer solution (0.01M) (ionic strength=0.15M), containing a concentration of NGF such that a protein titer equal to 0.02% in weight of the suspended microspheres is reached and such that the weight ratio of 1:1000 (NGF:gangliosides) is maintained. After 15 minutes of stirring with a semiautomatic system the container is immersed in liquid nitrogen until the suspension is completely frozen.

Once frozen, the suspension is freeze-dried for 24 hrs and the product stored at 4° C.

The mean particle size is 30 μm.

The quantities of incorporated NGF and GA are 20 ng and 20 μg respectively per milligram of microspheres.

EXAMPLE 19

A hyaluronic acid ester where all the carboxy groups of hyaluronic acid are esterified with dodecyl alcohol (HYAFF-73, as described in the U.S. Pat. No. 4,965,353), is dissolved in an aprotic solvent such as dimethylsulfoxide, at a concentration varying from 5 to 10% weight/volume, generally 7% w/v. Once the polymer has solubilized, to the solution are added a polypeptide, for example NGF at the predetermined concentration, for example 0.01% of the weight of the polymer mass, and a ganglioside mixture (Cronassial®) in a weight ratio of 1:1000 (NGF:Cronassial®). The mixture thus obtained will be referred to hereinafter as the discontinuous phase. At the same time a mixture is prepared in a suitable reactor of high-viscosity mineral oil containing Arlacel$^R$, a non-ionic surface-active agent, at a concentration of 1% w/v. This mixture will be referred to hereinafter as the continuous phase. It is kept at a temperature of 25° C. and stirred at a rate of 1000 RPM, while the discontinuous phase, prepared as previously described, is added to it.

In these conditions, emulsification of the two phases is instantaneous. The ratio between the two phases (discontinuous and continuous) is about 1 to 16.

After stirring for 15 minutes, ethyl acetate is added.

This solvent can be mixed perfectly with the two emulsion phases, but it is not a solvent for the polymer or the polypeptide (NGF) or the GA mixture (Cronassial®). It has been proven that the volume of extracting solvent needed to obtain complete extraction is two and a half times the total volume of the emulsion. To facilitate extraction, the stirring speed is set at 1400–1500 RPM for 10 minutes, then lowered to 500 RPM. The suspension thus obtained continues to be stirred, while being pumped by a screw pump through a filter press set at 1 atmosphere. Once this filtration is complete, it is pumped through a filter of normal-hexane, this being a solvent with the double action of "drying" the preparation and solubilizing any residue surfactant which may be present on the surface of the microspheres. The product is then put in suitable containers and stored at 4° C. In these working conditions the resulting mean particle size is 20 μm.

The quantities of incorporated NGF and GA are 10 ng and 10 μg, respectively, per milligram of microspheres.

EXAMPLE 20

A hyaluronic acid ester where all the carboxy groups of hyaluronic acid are esterified with benzyl alcohol (HYAFF-11, as described in the U.S. Pat. No. 4,965,353), is dissolved in an aprotic solvent such as dimethylsulfoxide, at a concentration varying from 5 to 10% weight/volume, generally 7% w/v. Once the polymer has solubilized, to the solution are added a polypeptide, for example NGF at a predetermined concentration, for example 0.01% of the weight of the polymer mass, and a monosialoganglioside GM1 in a weight ratio of 1:1000 (NGF:GM1).

The mixture thus obtained will be referred to hereinafter as the discontinuous phase. At the same time a mixture is prepared in a suitable reactor of high-viscosity mineral oil containing Arlacel$^R$, a non-ionic surface-active agent, at a concentration of 1% w/v.

This mixture will be referred to hereinafter as the continuous phase. It is kept at a temperature of 25° C. and stirred at a rate of 1000 RPM, while the discontinuous phase, prepared as previously described, is added to it.

In these conditions, emulsification of the two phases is instantaneous. The ratio between the two phases (discontinuous and continuous) is about 1 to 16.

After stirring for 15 minutes, ethyl acetate is added.

This solvent can be mixed perfectly with the two emulsion phases, but it is not a solvent for the polymer or the polipeptide (NGF) or the monosialoganglioside GM1. It has been proven that the volume of extracting solvent needed to obtain complete extraction is two and a half times the total volume of the emulsion. To facilitate extraction, the stirring speed is set at 1400–1500 RPM for 10 minutes, then lowered to 500 RPM. The suspension thus obtained continues to be stirred, while being pumped by a screw pump through a filter press set at 1 atmosphere. Once this filtration is complete, it is pumped through a filter of normal-hexane, a solvent with the double action of "drying" the preparation and solubilizing any residue surfactant which may be present on the surface of the microspheres. The product is then put in suitable containers and stored at 4° C.

In these working conditions, the resulting mean particle size is 10 μm. The quantities of NGF and monosialoganglioside GM1 are 10 ng and 10 μg, respectively, per milligram of microspheres.

EXAMPLE 21

A hyaluronic acid ester where all the carboxy groups of hyaluronic acid are esterified with ethyl alcohol (HYAFF-7, as described in the U.S. Pat. No. 4,965,353), is dissolved in an aprotic solvent such as dimethylsulfoxide, at a concentration varying from 5 to 10% weight/volume, generally 7% w/v. Once the polymer has solubilized, to the solution are added a polypeptide, for example NGF at a predetermined concentration, for example 0.01% of the weight of the polymer mass, and monosialoganglioside GM1 in a ratio of 1:1000 (NGF:GM1). This mixture will be referred to hereinafter as the discontinuous phase. At the same time a mixture is prepared in a suitable reactor of high-viscosity mineral oil containing Arlacel$^R$, a non-ionic surface-active agent, at a concentration of 1% w/v.

This mixture will be referred to hereinafter as the continuous phase. It is kept at a temperature of 25° C. and stirred at a rate of 1000 RPM, while the discontinuous phase, prepared as previously described, is added to it.

In these conditions, emulsification of the two phases is instantaneous. The ratio between the two phases (discontinuous and continuous) is about 1 to 16.

After stirring for 15 minutes, ethyl acetate is added.

This solvent can be mixed perfectly with the two emulsion phases, but it is not a solvent for the polymer, the polypeptide (NGF) or the monosialoganglioside GM1. It has been proven that the volume of extracting solvent needed to obtain complete extraction is two and a half times the total volume of the emulsion. To facilitate extraction, the stirring speed is set at 1400–1500 RPM for 10 minutes, then lowered to 500 RPM. The suspension thus obtained is stirred while being pumped by screw pump through a filter press set at 1 atmosphere. Once this filtration is complete, it is pumped through a filter of normal-hexane, this being a solvent with the double action of "drying" the preparation and solubilizing any residue surfactant which may be present on the surface of the microspheres. The product is then put in suitable containers and stored at 4° C.

The mean particle size is 30 $\mu$m.

The quantities of NGF and monosialoganglioside GM1 are 10 ng and 10 $\mu$g, respectively, per milligram of microspheres.

EXAMPLE 22

A hyaluronic acid ester where all the carboxy groups of hyaluronic acid are esterified with benzyl alcohol (HYAFF-11, as described in the U.S. Pat. No. 4,965,353), is dissolved in an aprotic solvent such as dimethylsulfoxide, at a concentration varying from 5 to 10% weight/volume, generally 7% w/v. Once the polymer has solubilized, a polypeptide, for example CNTF, at a predetermined concentration, for example 0.01% of the weight of the polymer mass, and a ganglioside mixture (Cronassial®) are added to the solution in a ratio of 1:1000 (CNTF:gangliosides). The mixture thus obtained will be referred to hereinafter as the discontinuous phase. At the same time a mixture is prepared in a suitable reactor of high-viscosity mineral oil containing Arlacel$^R$, a non-ionic surface-active agent, at a concentration of 1% w/v.

This mixture will be referred to hereinafter as the continuous phase. It is kept at a temperature of 25° C. and stirred at a rate of 1000 RPM, while the discontinuous phase, prepared as previously described, is added to it.

In these conditions, emulsification of the two phases is instantaneous. The ratio between the two phases (discontinuous and continuous) is about 1 to 16.

After stirring for 15 minutes, ethyl acetate is added.

This solvent can be mixed perfectly with the two emulsion phases, but it is not a solvent for the polymer or the polypeptide CNTF. It has been proven that the volume of extracting solvent needed to obtain complete extraction is two and a half times the total volume of the emulsion. To facilitate extraction, the stirring speed is set at 1400–1500 RPM for 10 minutes, then lowered to 500 RPM. The suspension thus obtained continues to be stirred, while being pumped by a screw pump through a filter press set at 1 atmosphere. Once this filtration is complete, it is pumped through a filter of normal-hexane, this being a solvent with the double action of "drying" the preparation and solubilizing any residue surfactant which may be present on the surface of the microspheres. The product is then put in suitable containers and stored at 4° C.

In these working conditions, the resulting mean particle size is 10 $\mu$m. The quantity of incorporated CNTF and GA is 10 ng and 10 $\mu$g, respectively, per milligram of microspheres.

EXAMPLE 23

A hyaluronic acid ester where all the carboxy groups of hyaluronic acid are esterified with benzyl alcohol (HYAFF-11, as described in the U.S. Pat. No. 4,965,353), is dissolved in an aprotic solvent such as dimethylsulfoxide, at a concentration varying from 5 to 10% weight/volume, generally 7% w/v. Once the polymer has solubilized, a ganglioside mixture at a predetermined concentration, for example 20% of the weight of the polymer, is added to the solution.

The solution obtained will be referred to hereinafter as the discontinuous phase. At the same time a mixture is prepared in a suitable reactor of high-viscosity mineral oil containing Arlacel$^R$, a non-ionic surface-active agent, at a concentration of 1% w/v.

This mixture will be referred to hereinafter as the continuous phase. It is kept at a temperature of 25° C. and stirred at a rate of 1000 RPM, while the discontinuous phase, prepared as previously described, is added to it.

In these conditions, emulsification of the two phases is instantaneous. The ratio between the two phases (discontinuous and continuous) is about 1 to 16.

After stirring for 15 minutes, ethyl acetate is added.

This solvent can be mixed perfectly with the two emulsion phases, but it is not a solvent for the polymer or the ganglioside mixture. It has been proven that the volume of extracting solvent needed to obtain complete extraction is two and a half times the total volume of the emulsion. To facilitate extraction the stirring rate was set at 1400–1500 RPM for 10 minutes, then lowered to 500 RPM. The suspension thus obtained continues to be stirred, while being pumped by a screw pump through a filter press set at 1 atmosphere. Once this filtration is complete, it is pumped through a filter of normal-hexane, this being a solvent with the double action of "drying" the preparation and solubilizing any residue surfactant which may be present on the surface of the microspheres. The product is then put in suitable containers and stored at 4° C.

The microspheres thus prepared are suspended in a phosphate buffer solution (0.01M) (ionic strength=0.15M) containing a concentration of CNTF such that a protein titer equal to 0.02% of the weight of the suspended microspheres is reached, and such that the weight ratio of 1:1000 (CNTF:gangliosides) is maintained. After 15 minutes of stirring with a semiautomatic system the container is immersed in liquid nitrogen until the suspension is completely frozen.

Once frozen, the suspension is freeze-dried for 24 hrs and the product stored at 4° C.

The mean particle size is 10 $\mu$m.

The quantities of incorporated CNTF and GA are 20 ng and 20 $\mu$g, respectively, per milligram of microspheres.

EXAMPLE 24

A hyaluronic acid ester where all the carboxy groups of hyaluronic acid are esterified with ethyl alcohol (HYAFF-7, as described in the U.S. Pat. No. 4,965,353), is dissolved in an aprotic solvent such as dimethylsulfoxide, at a concentration varying from 5 to 10% weight/volume, generally 7% w/v. Once the polymer has solubilized, a polypeptide, for example CNTF at a predetermined concentration, for example 0.01% of the weight of the polymer mass, and a ganglioside mixture (Cronassial®) in a weight ratio of 1:1000 (CNTF:Cronassial®) are added to the solution. The mixture thus obtained will be referred to hereinafter as the discontinuous phase. At the same time a mixture is prepared in a suitable reactor of high-viscosity mineral oil containing Arlacel$^R$, a non-ionic surface-active agent, at a concentration of 1% w/v.

This mixture will be referred to hereinafter as the continuous phase. It is kept at a temperature of 25° C. and stirred at a rate of 1000 RPM, while the discontinuous phase, prepared as previously described, is added to it.

In these conditions, emulsification of the two phases is instantaneous. The ratio between the two phases (discontinuous and continuous) is about 1 to 16.

After stirring for 15 minutes, ethyl acetate is added.

This solvent can be mixed perfectly with the two emulsion phases, but it is not a solvent for the polymer, the polypeptide (CNTF) or the GA mixture (Cronassial®). It has been proven that the volume of extracting solvent needed to obtain complete extraction is two and a half times the volume of the emulsion. To facilitate extraction, the stirring speed is set at 1400–1500 RPM for 10 minutes, then lowered to 500 RPM. The suspension thus obtained continues to be stirred, while being pumped by a screw pump through a filter press set at 1 atmosphere. Once this filtration is complete, it is pumped through a filter of normal-hexane, this being a solvent with the double action of "drying" the preparation and solubilizing any possible residues of surfactant which may be present on the surface of the microspheres. The product is then put in suitable containers and stored at 4° C.

The mean particle size is 30 $\mu$m.

The quantities of incorporated CNTF and GA are 10 ng and 10 $\mu$g, respectively, per milligram of microspheres.

EXAMPLE 25

A hyaluronic acid ester where all the carboxy groups of hyaluronic acid are esterified with ethyl alcohol (HYAFF-7, as described in the U.S. Pat. No. 4,965,353), is dissolved in an aprotic solvent such as dimethylsulfoxide, at a concentration varying from 5 to 10% weight/volume, generally 7% w/v. Once the polymer has solubilized, a ganglioside mixture (Cronassial®) at the predetermined concentration, for example 10% of the weight of the polymer, is added to the solution. The solution obtained will be referred to hereinafter as the discontinuous phase. At the same time a mixture is prepared in a suitable reactor of high-viscosity mineral oil containing Arlacel$^R$, a non-ionic surface-active agent, at a concentration of 1% w/v.

This mixture will be referred to hereinafter as the continuous phase. It is kept at a temperature of 25° C. and stirred at a rate of 1000 RPM, while the discontinuous phase, prepared as previously described, is added to it.

In these conditions, emulsification of the two phases is instantaneous. The ratio between the two phases (discontinuous and continuous) is about 1 to 16.

After stirring for 15 minutes, ethyl acetate is added.

This solvent can be mixed perfectly with the two emulsion phases, but it is not a solvent for the polymer or the ganglioside mixture. It has been proven that the volume of extracting solvent needed to obtain complete extraction is two and a half times the volume of the emulsion. To facilitate extraction, the stirring speed is set at 1400–1500 RPM for 10 minutes, then lowered to 500 RPM. The suspension thus obtained continues to be stirred, while being pumped by a screw pump through a filter press set at 1 atmosphere. Once this filtration is complete, it is passed through a normal-hexane filter, this being a solvent with the double action of "drying" the preparation and solubilizing any residue surfactant which may be present on the surface of the microspheres. The product is then put in suitable containers and stored at 4° C.

The microspheres thus prepared are suspended in a phosphate buffer solution (0.01M) (ionic strength 0.15 M), containing a concentration of CNTF such that a protein titer equal to 0.01% in weight of the suspended microspheres is reached and such that the weight ratio of 1:1000 (CNTF:gangliosides) is maintained. After 15 minutes of stirring with a semiautomatic system the container is immersed in liquid nitrogen until the suspension is completely frozen.

Once frozen, the suspension is freeze-dried for 24 hrs and the product stored at 4° C.

The mean particle size is 30 $\mu$m.

The quantities of incorporated CNTF and GA are 10 ng and 10 $\mu$g, respectively, per milligram of microspheres.

EXAMPLE 26

A hyaluronic acid ester where all the carboxy groups of hyaluronic acid are esterified with benzyl alcohol (HYAFF-11, as described in the U.S. Pat. No. 4,965,353), is dissolved in an aprotic solvent such as dimethylsulfoxide, at a concentration varying from 5 to 10% weight/volume, generally 7% w/v. Once the polymer has solubilized, a polypeptide, for example CNTF, at a predetermined concentration, for example 0.01% of the weight of the polymer mass, and the monosialoganglioside GM1 (Sygen) are added to the solution in a ratio of 1:1000 (CNTF:Sygen). The mixture thus obtained will be referred to hereinafter as the discontinuous phase. At the same time a mixture is prepared in a suitable reactor of high-viscosity mineral oil containing Arlacel$^R$, a non-ionic surface-active agent, at a concentration of 1% w/v.

This mixture will be referred to hereinafter as the continuous phase. It is kept at a temperature of 25° C. and stirred at a rate of 1000 RPM, while the discontinuous phase, prepared as previously described, is added to it.

In these conditions, emulsification of the two phases is instantaneous. The ratio between the two phases (discontinuous and continuous) is about 1 to 16.

After stirring for 15 minutes, ethyl acetate is added.

This solvent can be mixed perfectly with the two emulsion phases, but it is not a solvent for the polymer or the polypeptide CNTF or the monosialoganglioside GM1 (Sygen). It has been proven that the volume of extracting solvent needed to obtain complete extraction is two and a half times the total volume of the emulsion. To facilitate extraction, the stirring speed is set at 1400–1500 RPM for 10 minutes, then lowered to 500 RPM. The suspension thus obtained continues to be stirred, while being pumped by a screw pump through a filter press set at 1 atmosphere. Once this filtration is complete, it is pumped through a filter of normal-hexane, this being a solvent with the double action of "drying" the preparation and solubilizing any residue surfactant which may be present on the surface of the microspheres. The product is then put in suitable containers and stored at 4° C.

In these working conditions the resulting mean particle size is 10 $\mu$m. The quantity of incorporated CNTF and GM1 is 10 ng and 10 $\mu$g, respectively, per milligram of microspheres.

EXAMPLE 27

A hyaluronic acid ester where all the carboxy groups of hyaluronic acid are esterified with benzyl alcohol (HYAFF-11, as described in the U.S. Pat. No. 4,965,353), is dissolved in an aprotic solvent such as dimethylsulfoxide, at a concentration varying from 5 to 10% weight/volume, generally 7% w/v. Once the polymer has solubilized, a polypeptide, for example CNTF, at a predetermined concentration, for example 0.01% of the weight of the polymer mass, and inner esters of the ganglioside mixture (AGF1) are added to the solution in a ratio of 1:1000 (CNTF:AGF1). The mixture thus obtained will be referred to hereinafter as the discontinuous phase. At the same time a mixture is prepared in a suitable reactor of high-viscosity mineral oil containing Arlacel$^R$, a non-ionic surface-active agent, at a concentration of 1% w/v.

This mixture will be referred to hereinafter as the continuous phase. It is kept at a temperature of 25° C. and stirred at a rate of 1000 RPM, while the discontinuous phase, prepared as previously described, is added to it.

In these conditions, emulsification of the two phases is instantaneous. The ratio between the two phases (discontinuous and continuous) is about 1 to 16.

After stirring for 15 minutes, ethyl acetate is added.

This solvent can be mixed perfectly with the two emulsion phases, but it is not a solvent for the polymer or the polypeptide CNTF or the inner esters of the ganglioside mixture (AGF1). It has been proven that the volume of extracting solvent needed to obtain complete extraction is two and a half times the total volume of the emulsion. To facilitate extraction, the stirring speed is set at 1400–1500 RPM for 10 minutes, then lowered to 500 RPM. The suspension thus obtained continues to be stirred, while being pumped by a screw pump through a filter press set at 1 atmosphere. Once this filtration is complete, it is pumped through a filter of normal-hexane, this being a solvent with the double action of "drying" the preparation and solubilizing any residue surfactant which may be present on the surface of the microspheres. The product is then put in suitable containers and stored at 4° C.

In these working conditions the resulting mean particle size is 10 $\mu$m. The quantity of incorporated CNTF and AGF1 is 10 ng and 10 $\mu$g, respectively, per milligram of microspheres.

EXAMPLE 28

A hyaluronic acid ester where all the carboxy groups of hyaluronic acid are esterified with benzyl alcohol (HYAFF-11, as described in the U.S. Pat. No. 4,965,353), is dissolved in an aprotic solvent such as dimethylsulfoxide, at a concentration varying from 5 to 10% weight/volume, generally 7% w/v. Once the polymer has solubilized, a polypeptide, for example CNTF, at a predetermined concentration, for example 0.01% of the weight of the polymer mass, and the monosialoganglioside GM1 inner ester (AGF2) are added to the solution in a ratio of 1:1000 (CNTF:AGF2). The mixture thus obtained will be referred to hereinafter as the discontinuous phase. At the same time a mixture is prepared in a suitable reactor of high-viscosity mineral oil containing Arlacel$^R$, a non-ionic surface-active agent, at a concentration of 1% w/v.

This mixture will be referred to hereinafter as the continuous phase. It is kept at a temperature of 25° C. and stirred at a rate of 1000 RPM, while the discontinuous phase, prepared as previously described, is added to it. In these conditions, emulsification of the two phases is instantaneous. The ratio between the two phases (discontinuous and continuous) is about 1 to 16.

After stirring for 15 minutes, ethyl acetate is added.

This solvent can be mixed perfectly with the two emulsion phases, but it is not a solvent for the polymer or the polypeptide CNTF or the monosialoganglioside GM1 inner ester (AGF2). It has been proven that the volume of extracting solvent needed to obtain complete extraction is two and a half times the total volume of the emulsion. To facilitate extraction, the stirring speed is set at 1400–1500 RPM for 10 minutes, then lowered to 500 RPM. The suspension thus obtained continues to be stirred, while being pumped by a screw pump through a filter press set at 1 atmosphere. Once this filtration is complete, it is pumped through a filter of normal-hexane, this being a solvent with the double action of "drying" the preparation and solubilizing any residue surfactant which may be present on the surface of the microspheres. The product is then put in suitable containers and stored at 4° C.

In these working conditions the resulting mean particle size is 10 $\mu$m. The quantity of incorporated CNTF and AGF2 is 10 ng and 10 $\mu$g, respectively, per milligram of microspheres.

EXAMPLE 29

A hyaluronic acid ester where all the carboxy groups of hyaluronic acid are esterified with benzyl alcohol (HYAFF-11, as described in the U.S. Pat. No. 4,965,353), is dissolved in an aprotic solvent such as dimethylsulfoxide, at a concentration varying from 5 to 10% weight/volume, generally 8% w/v. Once the polymer has solubilized, to this is added a solution of GM1 at a predetermined concentration, for example 20% of the weight of the polymer mass. The solution thus obtained will be referred to hereinafter as the discontinuous phase. At the same time a mixture is prepared in a suitable reactor of high-viscosity mineral oil containing Arlacel$^R$, a non-ionic surface-active agent, at a concentration of 1% w/v.

This mixture will be referred to hereinafter as the continuous phase. It is kept at a temperature of 25° C. and stirred at a rate of 700 RPM, while the discontinuous phase, prepared as previously described, is added to it.

In these conditions, emulsification of the two phases is instantaneous. The ratio between the two phases (discontinuous and continuous) is about 1 to 16.

After stirring for 15 minutes, ethyl acetate is added.

This solvent can be mixed perfectly with the two emulsion phases, but it is not a solvent for the polymer. It has been proven that the volume of extracting solvent needed to obtain complete extraction is two and a half times the total volume of the emulsion. To facilitate extraction, the stirring speed is set at 1400–1500 RPM for 10 minutes, then lowered to 500 RPM. The suspension thus obtained continues to be stirred, while being pumped by a screw pump through a filter press set at 1 atmosphere. Once this filtration is complete, it is pumped through a filter of normal-hexane, this being a solvent with the double action of "drying" the preparation and solubilizing any residue surfactant which may be present on the surface of the microspheres. The product is then put in suitable containers and stored at 4° C. In these working conditions the resulting mean particle size is 40 $\mu$m. The quantity of incorporated $GM_1$ is 180 $\mu$g per milligram of microspheres.

EXAMPLE 30

A hyaluronic acid ester where all the carboxy groups of hyaluronic acid are esterified with benzyl alcohol (HYAFF-11, as described in the U.S. Pat. No. 4,965,353), is dissolved in an aprotic solvent such as dimethylsulfoxide, at a concentration varying from 5 to 10% weight/volume, generally 8% w/v. Once the polymer has solubilized, to this is added a solution of GM1 at a predetermined concentration, for example 20% of the weight of the polymer mass. The mixture thus obtained will be referred to hereinafter as the discontinuous phase. At the same time a mixture is prepared in a suitable reactor of high-viscosity mineral oil containing Arlacel$^R$, a non-ionic surface-active agent, at a concentration of 1% w/v. This mixture will be referred to hereinafter as the continuous phase. It is kept at a temperature of 25° C. and stirred at a rate of 1000 RPM, while the discontinuous phase, prepared as previously described, is added to it.

In these conditions, emulsification of the two phases is instantaneous. The ratio between the two phases (discontinuous and continuous) is about 1 to 16.

After stirring for 15 minutes, ethyl acetate is added.

This solvent can be mixed perfectly with the two emulsion phases, but it is not a solvent for the polymer. It has been proven that the volume of extracting solvent needed to obtain complete extraction is two and a half times the total volume of the emulsion. To facilitate extraction, the stirring speed is set at 1400–1500 RPM for 10 minutes, then lowered to 500 RPM. The suspension thus obtained continues to be stirred, while being pumped by a screw pump through a filter press set at 1 atmosphere. Once this filtration is complete, it is pumped through a filter of normal-hexane, this being a solvent with the double action of "drying" the preparation and solubilizing any residue surfactant which may be present on the surface of the microspheres. The product is then put in suitable containers and stored at 4° C. In these working conditions the resulting mean particle size is 10 $\mu$m. The quantity of incorporated $GM_1$ is 180 $\mu$g per milligram of microspheres.

EXAMPLE 31

A hyaluronic acid ester where all the carboxy groups of hyaluronic acid are esterified with benzyl alcohol (HYAFF-11, as described in the U.S. Pat. No. 4,965,353) is dissolved in an aprotic solvent such as dimethylsulfoxide at a concentration varying from 5 to 10% weight/volume, generally 7% w/v. The solution obtained will be referred to hereinafter as the discontinuous phase. At the same time a mixture is prepared in a suitable reactor of high-viscosity mineral oil containing Arlacel$^R$, a non-ionic surface-active agent, at a concentration of 1% w/v.

This mixture will be referred to hereinafter as the continuous phase. It is kept at a temperature of 25° C. and stirred at a rate of 1000 RPM, while the discontinuous phase, prepared as previously described, is added to it. In these conditions, emulsification of the two phases is instantaneous.

The ratio between the two phases (discontinuous and continuous) is about 1 to 16.

After stirring for 15 minutes, ethyl acetate is added.

This solvent can be mixed perfectly with the two emulsion phases, but it is not a solvent for the polymer. It has been proven that the volume of extracting solvent needed to obtain complete extraction the total volume of the emulsion, in order to obtain complete extraction. To facilitate extraction, the stirring speed is set at 1400–1500 for 10 minutes, then lowered to 500 RPM. The suspension thus obtained continues to be stirred, while being pumped by a screw pump through a filter press set at 1 atmosphere. Once this filtration is complete, it is pumped through a filter of normal-hexane, this being a solvent with the double action of "drying" the preparation and solubilizing any residue surfactant which may be present on the surface of the microspheres. The product is then put in suitable containers and stored at 4° C.

The microspheres thus prepared are suspended in a phosphate buffer solution (0.01M), containing a concentration of immunoglobulin such that a protein titer of 3 $\mu$g per mg of suspended microspheres is reached. After 15 minutes of stirring with a semiautomatic system the container is immersed in liquid nitrogen until the suspension is completely frozen.

Once frozen, the suspension is freeze-dried for 24 hrs and the product stored at 4° C.

The mean particle size is 10 $\mu$m.

The quantity of incorporated immunoglobulin is 2.5 $\mu$g per mg of microspheres.

EXAMPLE 32

A hyaluronic acid ester where all the carboxy groups of hyaluronic acid are esterified with benzyl alcohol (HYAFF-11, as described in the U.S. Pat. No. 4,965,353), is dissolved in an aprotic solvent such as dimethylsulfoxide, at a concentration varying from 5 to 10% weight/volume, generally 7% w/v. Once the polymer has solubilized, a polypeptide, for example calcitonin, dissolved in hydrochloric acid at pH=3, at the predetermined concentration, for example 15 I.U. per mg of polymer, is added to the solution. The mixture thus obtained will be referred to hereinafter as the discontinuous phase. At the same time a mixture is prepared in a suitable reactor of high-viscosity mineral oil containing Arlacel$^R$, a non-ionic surface-active agent, at a concentration of 1% w/v.

This mixture will be referred to hereinafter as the continuous phase. It is kept at a temperature of 25° C. and stirred at a rate of 1000 RPM, while the discontinuous phase, prepared as previously described, is added to it.

In these conditions, emulsification of the two phases is instantaneous. The ratio between the two phases (discontinuous and continuous) is about 1 to 16.

After stirring for 15 minutes, ethyl acetate is added.

This solvent can be mixed perfectly with the two emulsion phases, but it is not a solvent for the polymer or the polypeptide calcitonin. It has been proven that the volume of extracting solvent needed to obtain complete extraction is two and a half times the total volume of the emulsion. To facilitate extraction, the stirring speed is set at 1400–1500 RPM for 10 minutes, then lowered to 500 RPM. The suspension thus obtained continues to be stirred, while being pumped by a screw pump through a filter press set at 1 atmosphere. Once this filtration is complete, it is pumped through a filter of normal-hexane, this being a solvent with the double action of "drying" the preparation and solubilizing any residue surfactant which may be present on the surface of the microspheres. The product is then put in suitable containers and stored at 4° C.

In these working conditions the resulting mean particle size is 10 $\mu$m. The quantity of incorporated calcitonin is 13 I.U. per mg of microspheres.

EXAMPLE 33

A hyaluronic acid ester where all the carboxy groups of hyaluronic acid are esterified with benzyl alcohol (HYAFF-11, as described in the U.S. Pat. No. 4,965,353), is dissolved in an aprotic solvent such as dimethylsulfoxide, at a concentration varying from 5 to 10% weight/volume, generally 7% w/v. The solution obtained will be referred to hereinafter as the discontinuous phase. At the same time a mixture is prepared in a suitable reactor of high-viscosity mineral oil containing Arlacel$^R$, a non-ionic surface-active agent, at a concentration of 1% w/v.

This mixture will be referred to hereinafter as the continuous phase. It is kept at a temperature of 25° C. and stirred at a rate of 1000 RPM, while the discontinuous phase, prepared as previously described, is added to it.

In these conditions, emulsification of the two phases is instantaneous. The ratio between the two phases (discontinuous and continuous) is about 1 to 16.

After stirring for 15 minutes, ethyl acetate is added.

This solvent can be mixed perfectly with the two emulsion phases, but it is not a solvent for the polymer. It has been proven that the volume of extracting solvent needed to obtain complete extraction is two and a half times the total volume of the emulsion. To facilitate extraction, the stirring rate is set at 1400–1500 RPM for 10 minutes, then lowered to 500 RPM. The suspension thus obtained is stirred while being pumped through a screw pump through a filter press set at 1 atmosphere. Once this filtration is complete, it is pumped through a filter of normal-hexane, this being a solvent with the double action of "drying" the preparation and solubilizing any residue surfactant which may be present on the surface of the microspheres. The product is then put in suitable containers and stored at 4° C.

The microspheres thus prepared are suspended in a phosphate buffer solution (0.01M) (ionic strength=0.1M) at pH=7, containing a concentration of calcitonin such that a protein titer of 15 I.U. per mg of suspended microspheres is reached. After 15 minutes of stirring with a semiautomatic system the container is immersed in liquid nitrogen until the suspension is completely frozen.

Once frozen, the suspension is freeze-dried for 24 hrs and the product stored at 4° C. The mean particle size is 10 $\mu$m. The quantity of incorporated calcitonin is 13 IU/mg of microspheres.

EXAMPLE 34

A hyaluronic acid ester where 75% of the carboxy groups of hyaluronic acid are esterified with benzyl alcohol while the remaining part is salified with sodium (HYAFF-11 p75, as described in the U.S. Pat. No. 4,965,353), is dissolved in an aprotic solvent such as dimethylsulfoxide at a concentration varying from 5 to 10% weight/volume, generally 7% w/v. Once the polymer has solubilized, a polypeptide, for example calcitonin, dissolved in hydrochloric acid at pH=3, at a predetermined concentration, for example 15 I.U. per mg of polymer is added to the solution. The mixture thus obtained will be referred to hereinafter as the discontinuous phase. At the same time a mixture is prepared in a suitable reactor of high-viscosity mineral oil containing Arlacel$^R$, a non-ionic surface-active agent, at a concentration of 1% w/v.

This mixture will be referred to hereinafter as the continuous phase. It is kept at a temperature of 25° C. and stirred at a rate of 1000 RPM, while the discontinuous phase, prepared as previously described, is added to it.

In these conditions, emulsification of the two phases is instantaneous. The ratio between the two phases (discontinuous and continuous) is about 1 to 16.

After stirring for 15 minutes, ethyl acetate is added.

This solvent can be mixed perfectly with the two emulsion phases, but it is not a solvent for the polymer or the polipeptide calcitonin. It has been proven that the volume of extracting solvent needed to obtain complete extraction is two and a half times the total volume of the emulsion. To facilitate extraction, the stirring speed is set at 1400–1500 RPM for 10 minutes, then lowered to 500 RPM. The suspension thus obtained continues to be stirred, while being pumped by a screw pump through a filter press set at 1 atmosphere. Once this filtration is complete, it is pumped through a filter of normal-hexane, this being a solvent with the double action of "drying" the preparation and solubilizing any residue surfactant which may be present on the surface of the microspheres. The product is then put in suitable containers and stored at 4° C.

The mean particle size is 15 $\mu$m. The quantity of incorporated calcitonin is 13 I.U per mg of microspheres.

EXAMPLE 35

A hyaluronic acid ester where all the carboxy groups of hyaluronic acid are esterified with ethyl alcohol (HYAFF-7, as described in the U.S. Pat. No. 4,965,353), is dissolved in an aprotic solvent such as dimethylsulfoxide at a concentration varying from 5 to 10% weight/volume, generally 7% w/v. Once the polymer has solubilized, a polypeptide, for example calcitonin, dissolved in hydrochloric acid at pH=3, at a predetermined concentration, for example 15 I.U. per mg of polymer, is added to the solution. The mixture thus obtained will be referred to hereinafter as the discontinuous phase. At the same time a mixture is prepared in a suitable reactor of high-viscosity mineral oil containing Arlacel$^R$, a non-ionic surface-active agent, at a concentration of 1% w/v.

This mixture will be referred to hereinafter as the continuous phase. It is kept at a temperature of 25° C. and stirred at a rate of 1000 RPM, while the discontinuous phase, prepared as previously described, is added to it.

In these conditions, emulsification of the two phases is instantaneous. The ratio between the two phases (discontinuous and continuous) is about 1 to 16.

After stirring for 15 minutes, ethyl acetate is added.

This solvent can be mixed perfectly with the two emulsion phases, but it is not a solvent for the polymer or the polipeptide calcitonin. It has been proven that the volume of extracting solvent needed to obtain complete extraction is two and a half times the total volume of the emulsion. To facilitate extraction, the stirring speed is set at 1400–1500 RPM for 10 minutes, then lowered to 500 RPM. The suspension thus obtained continues to be stirred, while being pumped by a screw pump through a filter press set at 1 atmosphere. Once this filtration is complete, it is pumped through a filter of normal-hexane, this being a solvent with the double action of "drying" the preparation and solubilizing any residue surfactant which may be present on the surface of the microspheres. The product is then put in suitable containers and stored at 4° C.

The mean particle size is 30 $\mu$m. The quantity of incorporated calcitonin is 13 I.U. per mg of microspheres.

EXAMPLE 36

A hyaluronic acid ester where all the carboxy groups of hyaluronic acid are esterified with ethyl alcohol (HYAFF-7, as described in the U.S. Pat. No. 4,965,353), is dissolved in an aprotic solvent such as dimethylsulfoxide at a concentration varying from 5 to 10% weight/volume, generally 7% w/v. The solution thus obtained will be referred to hereinafter as the discontinuous phase. At the same time a mixture is prepared in a suitable reactor of high-viscosity mineral oil containing Arlacel$^R$, a non-ionic surface-active agent, at a concentration of 1% w/v.

This mixture will be referred to hereinafter as the continuous phase. It is kept at a temperature of 25° C. and stirred at a rate of 1000 RPM, while the discontinuous phase, prepared as previously described, is added to it. In these conditions, emulsification of the two phases is instantaneous. The ratio between the two phases (discontinuous and continuous) is about 1 to 16.

After stirring for 15 minutes, ethyl acetate is added.

This solvent can be mixed perfectly with the two emulsion phases, but it is not a solvent for the polymer. It has been proven that the volume of extracting solvent needed to obtain complete extraction is two and a half times the total volume of the emulsion. To facilitate extraction, the stirring speed is set at 1400–1500 for 10 minutes, then lowered to 500 RPM. The suspension thus obtained continues to be stirred, while being pumped by a screw pump through a filter press set at 1 atmosphere. Once this filtration is complete, it is pumped through a filter of normal-hexane, this being a solvent with the double action of "drying" the preparation and solubilizing any residue surfactant which may be present on the surface of the microspheres. The product is then put in suitable containers and stored at 4° C. The microspheres thus prepared are suspended in a phosphate buffer solution (0.01M) (ionic strength 0.1M) at pH=7, containing a concentration of calcitonin such that a protein titer of 15 I.U. per mg of suspended microspheres is reached. After 15 minutes of stirring with a semiautomatic system the container is immersed in liquid nitrogen until the suspension is completely frozen.

Once frozen, the suspension is freeze-dried for 24 hrs and the product stored at 4° C.

The mean particle size is 30 $\mu$m. The quantity of incorporated calcitonin is 13 I.U. per mg of microspheres.

EXAMPLE 37

Microspheres were prepared containing different concentrations of calcitonin, mainly between $5 \times 10^{-3}$ and 10 I.U. per mg of microspheres, with different hyaluronic acid derivatives. Polymers with different degrees of hydrophobicity were used. The following are reported as examples:

HYAFF-11 (HA totally esterified with benzyl alcohol)

HYAFF-11 p75 (HA partially esterified with benzyl alcohol)

HYAFF-7 (HA totally esterified with ethyl alcohol)

The microspheres were prepared as reported in Examples 32-33-34-35-36, and tested in an in vivo animal model for the subcutaneous absorption of calcitonin. In this animal model, formulations were tested with the protein, either incorporated internally in the polymer matrix, or adsorbed externally on the surface of the microspheres. The formulations were known as:

Formulation 1: microspheres of HYAFF-11 containing calcitonin physically incorporated at a concentration of $5 \times 10^{-3}$ I.U. per mg of microspheres Formulation 2: microspheres of HYAFF-11 containing calcitonin adsorbed on their surface at a concentration of $5 \times 10^{-3}$ I.U. per mg of powder.

Formulation 3: microspheres of HYAFF-11 p75 containing calcitonin physically incorporated at a concentration of $5 \times 10^{-3}$ I.U. per mg of microspheres.

Formulation 4: microspheres of HYAFF-7 containing calcitonin adsorbed on their surface at a concentration of $5 \times 10^{-3}$ I.U. per mg of powder.

Formulation 5: buffered solution containing calcitonin at a concentration of $5 \times 10^{-3}$ I.U.

The microspheres were administered to male Wistar rats (115–125 gr) by subcutaneous route. The rats were not fed for 20 hrs before the experiment. For each formulation, 30 mg of microspheres were suspended in 20 ml of diluting solution, composed of a mixture of 425 ml of sodium acetate (1%) and 31.25 ml of 16% gelatin brought to pH 4.00 with HCl 1N. Subsequently, 0.4 ml (3 m I.U.) of each formulation were injected subcutaneously.

At fixed times of 1, 2, 3, 4 and 5 hrs after administration, 3 ml of blood were drawn from the abdominal aorta, and the animal was sacrificed. Blood calcium was then determined directly on the serum by atomic absorption.

Table 1 shows the decrease in blood calcium values over time for all the formulations tested. From this table it is possible to see that the polymer has a clear delaying effect on calcitonin release, which has evident repercussions on the times and behaviour of the Ca++ decrease in the blood.

TABLE 1

| Formulation | Blood $Ca^{+2}$ decrease (%) at different times (hrs) | | | | |
|---|---|---|---|---|---|
| | 1 | 2 | 3 | 4 | 5 |
| HYAFF-11 (int) | 5 | 18 | 30 | 27 | 13 |
| HYAFF-11 (ext) | 10 | 30 | 26 | 21 | 10 |
| HYAFF-11p75 (int) | 10 | 30 | 28 | 15 | 3 |
| HYAFF-7 (ext) | 12 | 28 | 24 | 17 | 2.8 |
| Calcitonin sol. | 30 | 22 | 15 | 10 | 2.5 |

The results also show that there is an effect due to the type of incorporation, where in the case of microspheres containing calcitonin physically incorporated in the polymer matrix the release is slower.

EXAMPLE 38

Microspheres were prepared which contained calcitonin at various concentrations, mainly $5 \times 10^{-3}$ and 10 I.U. per mg of microspheres) with different hyaluronic acid derivatives. Polymers with different degrees of hydrophobicity were used.

The following are examples:

HYAFF-11 (HA totally esterified with benzyl alcohol)

HYAFF-11 p75 (HA partially esterified with benzyl alcohol)

In the animal model devised to study vaginal absorption, formulations were tested having the protein incorporated within the microspheres or externally adsorbed on their surfaces.

The formulations were coded as follows:

HYAFF-11: microspheres containing calcitonin incorporated internally at a concentration of 5 I.U. per mg of microspheres.

HYAFF-11 p75: microspheres containing calcitonin incorporated internally at a concentration of 5 I.U. per mg of microspheres.

Calcitonin: calcitonin dissolved in 0.9% saline brought to pH 4 with hydrochloric acid at a concentration of 100 I.U./ml.

The above formulations were administered to female, oophorectomized, Wistar rats weighing 150–200 gr. The rats were anesthetized and tracheotomized. The carotid artery and the jugular vein were catheterized to allow blood withdrawal and replacement with saline at the established times.

The calcitonin solution was instilled into the vagina at a dose of 400 ul/kg, equal to 100 I.U./kg. The same volume of saline, pH=4, in the absence of calcitonin, was administered to a group of control rats.

The microspheres were administered at a dose of 100 I.U. 20 mg/kg by inserting a catheter into the vagina and spraying the microspheres in dry powder form.

The blood samples were gathered in heparin-treated containers and the plasma, obtained by centrifugation, was stored at −20° C. until analysis.

The concentration of calcium in the plasma was measured by spectroscopy in atomic absorption and expressed as a percentage of the initial concentration in the plasma.

FIG. 1 shows the decline in blood calcium after vaginal administration of 100 I.U. calcitonin. A decrease can be seen in blood plasma after 15 minutes while the maximum hypocalcemic effect is reached after 2 or 3 hours.

Figure 2:
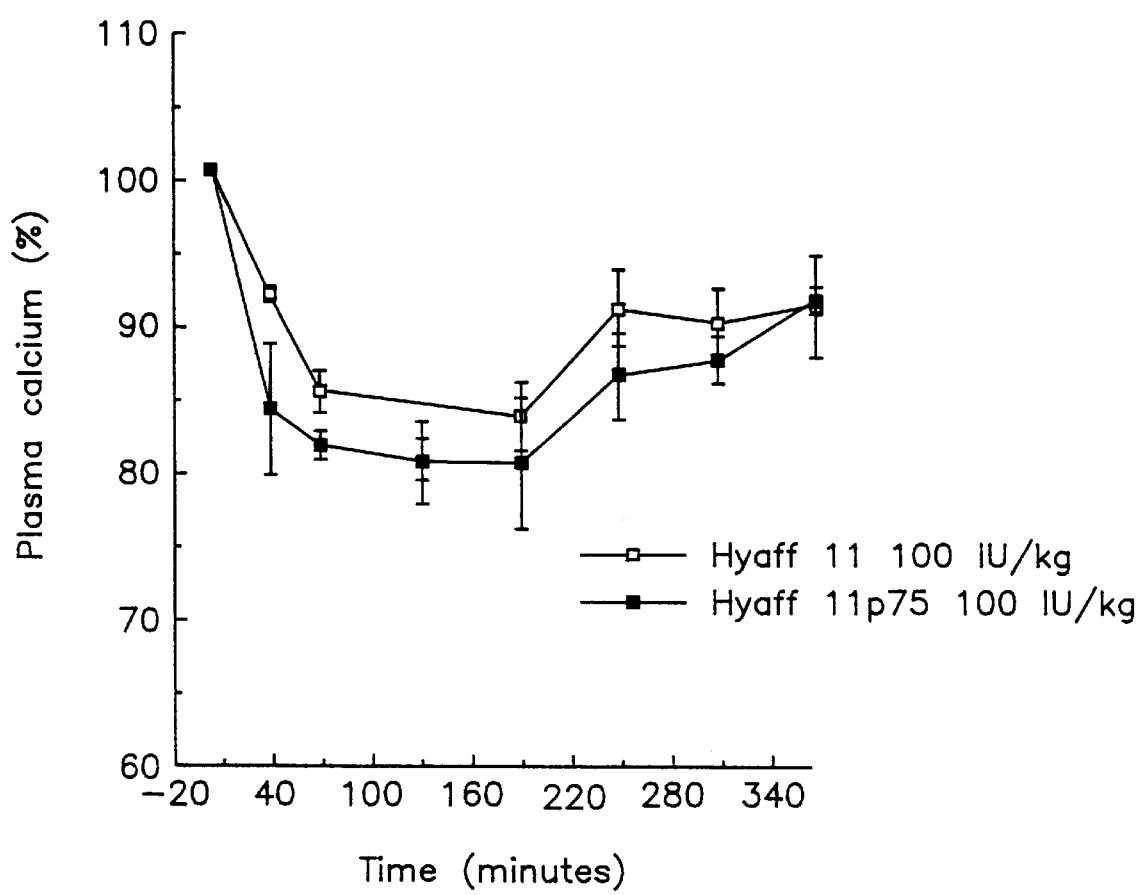
FIG. 2 shows the levels of calcium in plasma (%) after vaginal administration of calcitonin associated with mircospheres of HYAFF-11 and HYAFF-11 p75.

The small standard deviation revealed only slight animal-to-animal variability. FIG. 2 shows calcium levels in the plasma after vaginal administration of calcitonin formulated in HYAFF-11 and HYAFF-11 p75 microspheres.

Both formulations proved effective in absorbing blood calcium, indicating that the protein had not undergone degradation in the process of preparation of the microspheres.

The difference in plasma profiles obtained with the two formulations can be attributed to the different chemical-physical characteristics of the polymeric matrix.

The release of calcitonin from the microspheres and consequently its activity is slower in the case of HYAFF-11, where the polymer is totally esterified with benzyl alcohol, than in the case of HYAFF-11 p75. In this case the polypeptide was incorporated in a partially esterified matrix which, in the presence of the biological fluids, is hydrated more rapidly than the totally esterified polymer, and consequently the calcitonin spreads more quickly through the polymeric matrix into the vaginal mucosa.

The release of calcitonin can, therefore, be modulated according to the degree of esterification of the polymer.

EXAMPLE 39

Microspheres containing insulin were prepared and tested in an in vivo model.

The preparations of Na-insulin were administered through the nose to sheep, both as free insulin in solution and in association with hyaluronic acid derivatives in the form of microspheres prepared as reported in Examples 1-2-3-4-5.

To administer the solution, a 35-cm tube was inserted into the nasal cavity, taking care to place it at the set depth of 10 cm from the opening of the nostril.

For the administration of formulations in powder form, a 6.5-μm intratracheal tube was filled with the established dose of microspheres and placed in the nostril. In this case the device was placed at a depth of 6 cm from the opening of the nostril. Insulin was administered 2 I.U./Kg by intranasal route both in solution and associated with microspheres. Groups of four sheep were used for each experiment. The following formulations were prepared:

Formulation 1: for nasal administration of insulin associated with hyaluronic acid (HYAFF-11) microspheres a freeze-dried product was prepared (2.0 mg/kg corresponding to 2 I.U. insulin).

Formulation 2: for nasal administration of insulin associated with microspheres of hyaluronic acid (HYAFF-11 p75) a freeze-dried product was prepared (2.0 mg/kg corresponding to 2 I.U. insulin).

Formulation 3: for nasal administration of insulin associated with microspheres of hyaluronic acid (HYAFF-7) a freeze-dried product was prepared (2.0 mg/kg corresponding to 2 I.U. insulin).

Formulation 4: for nasal administration to controls a freeze-dried product was prepared of microspheres alone (HYAFF-11) (2.0 mg/kg).

Formulation 5: for nasal administration of insulin in aqueous solution a solution at a concentration of 2 I.U./ml was prepared.

At the set times, a 5-ml sample of blood was taken each previously cannulated jugular vein. Each blood sample was divided in half, 2.5 ml was placed in a heparin-treated test tube for insulin analysis, while for glycemia analysis the other 2.5 ml was placed in a test tube containing fluoride oxalate.

Table 2 shows the lowering of the plasma levels of glucose obtained after nasal administration of insulin.

| Formulation | Blood glucose decrease (%) at different times (min) | | | | | | | | | |
|---|---|---|---|---|---|---|---|---|---|---|
| | 10 | 20 | 30 | 40 | 60 | 80 | 90 | 120 | 140 | 190 |
| 1 | 7 | 15 | 25 | 40 | 65 | 60 | 51 | 42 | 21 | 7 |
| 2 | 10 | 20 | 39 | 58 | 49 | 30 | 21 | 7 | 0 | 0 |
| 3 | 12 | 19 | 35 | 57 | 40 | 29 | 18 | 5 | 0 | 0 |
| 4 | 0 | 0 | 0 | 0 | 0 | 0 | 0 | 0 | 0 | 0 |
| 5 | 4 | 6 | 8 | 7 | 6 | 0 | 0 | 0 | 0 | 0 |

It can be clearly seen from Table 2 that insulin administered through the nose as a simple solution (Formulation 5) has no significant effect on the lowering of blood glucose levels. It is possible to note a different profile in the lowering of blood glucose levels according to the type of hyaluronic acid ester used to prepare the micropheres. The microspheres made with HYAFF-7 (the most hydrophilic derivative) have a less "active" interaction with the nasal mucosa and consequently less effect on the lowering of blood glucose levels (Formulation 3).

The microspheres made with HYAFF-11 p75 (Formulation HYAFF-11 (Formulation 1) on the other hand, have a more marked interaction with the mucosal cells and in this case too the decrease in glycemia is correlated with the type of derivative: HYAFF-11 p75 has less effect than HYAFF-11, showing that the derivative's chemical-physical characteristics can pilot the release of the protein.

EXAMPLE 40

The preparations of Na-insulin were administered through the nose to sheep, both as free insulin in solution and in association with hyaluronic acid derivatives in the form of microspheres prepared as reported in Examples 1-2-3-4-5.

To administer the solution, a 35-cm tube was inserted into the nasal cavity, taking care to place it at the set depth of 10 cm from the opening of the nostril.

For the administration of formulations in powder form, a 6.5-μm intratracheal tube was filled with the established dose of microspheres and placed in the nostril. In this case the device was placed at a depth of 6 cm from the opening of the nostril. Insulin associated with microspheres of HYAFF-11 was administered by intranasal route at doses of 1-2-4-8 I.U./Kg. Groups of four sheep (about 40 kg) were used for each experiment. The following formulations were prepared:

1) HYAFF 11 containing insulin at a concentration of 1 I.U./mg of microspheres
2) HYAFF 11 containing insulin at a concentration of 2 I.U./mg of microspheres
3) HYAFF-11 containing insulin at a concentration of 4 I.U./mg of microspheres
4) HYAFF-11 containing insulin at a concentration of 8 I.U./mg of microspheres Each sheep in each group was treated with a dose of 2 I.U./kg of insulin associated with different quantities of microspheres.

At the set times, a 5-ml sample of blood was taken from each previously cannulated jugular vein. Each blood sample was divided in half, 2.5 ml was placed in a heparin-treated test tube for insulin analysis, while for glycemia analysis the other 2.5 ml was placed in a test tube containing fluoride oxalate.

Figure 3:
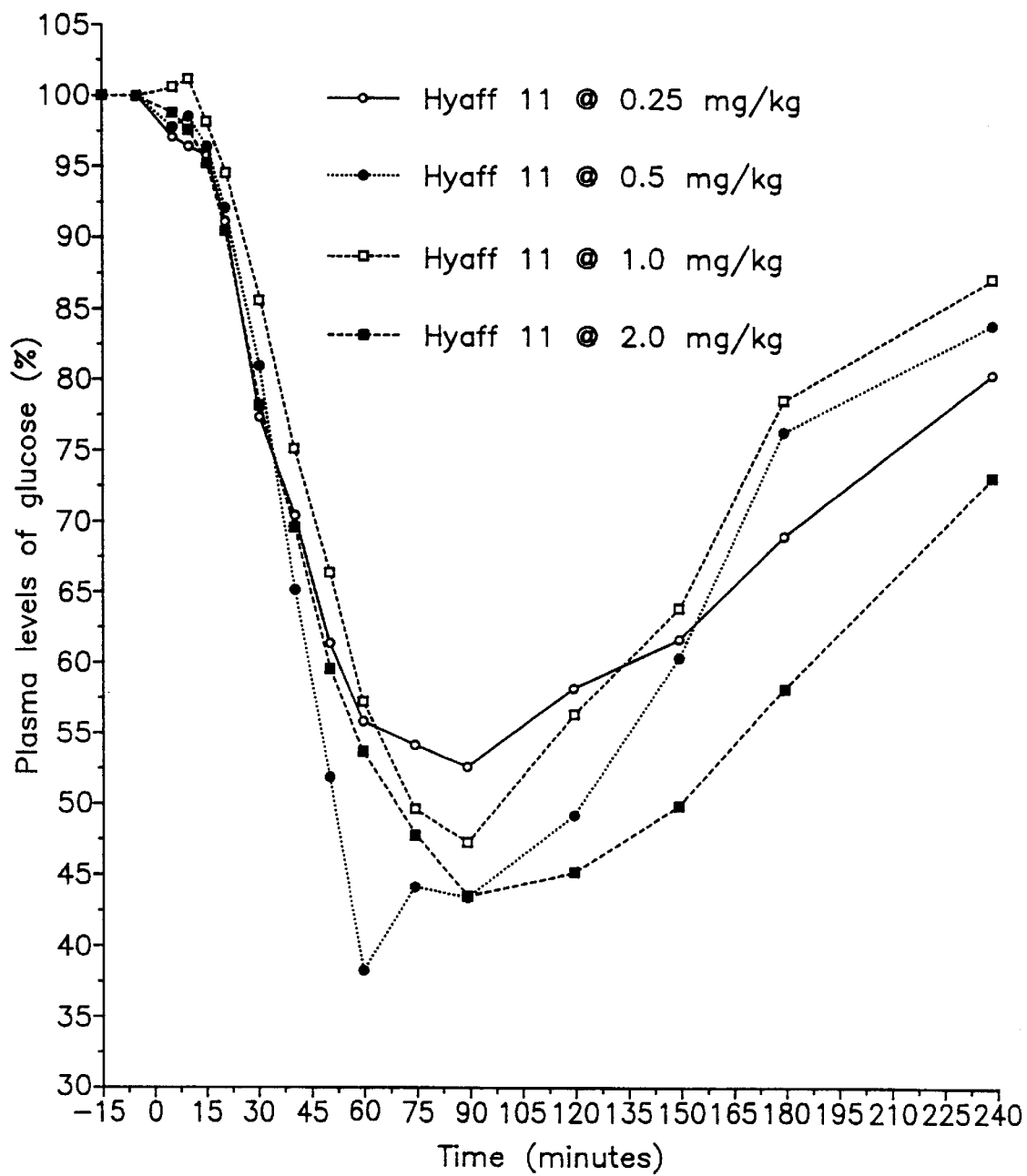
FIG. 3 shows the effect of different doses of HYAFF-11 microspheres containing insulin on plasma glucose decrease after nasal administration in sheep.

FIG. 3 shows mean values of the blood glucose concentrations after administration of 2.0 I.U./kg of insulin associated with 2.0-1.0-0.5 or 0.25 mg/kg of HYAFF-11.

These results show that all the formulations cause a marked decrease in glycemia and that the profile of this decrease was similar for each nasal administration.

Figure 4:
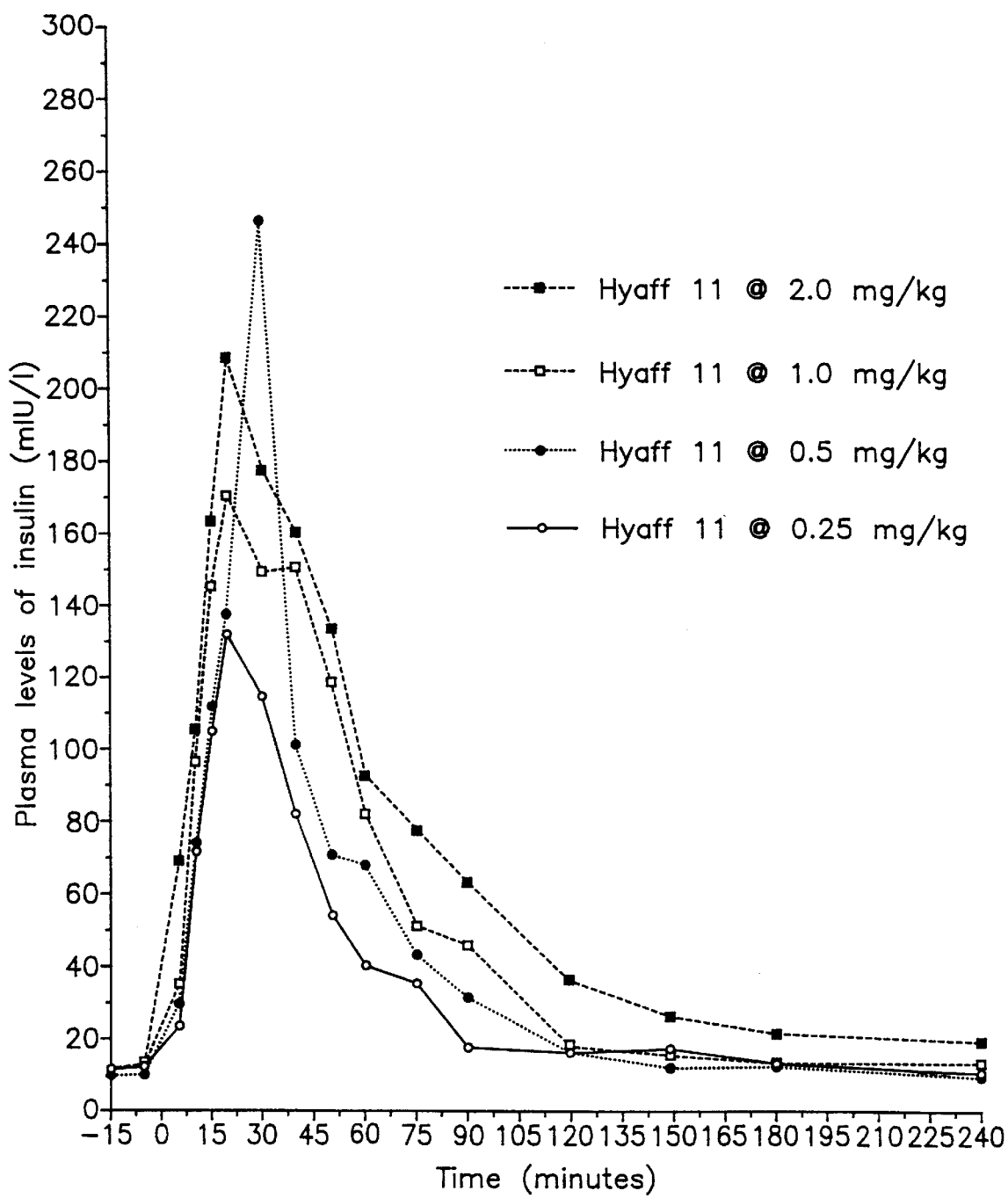
FIG. 4 shows the levels of insulin in plasma after nasal administration to sheep of different doses of HYAFF-11 microspheres.

FIG. 4 shows insulin levels in plasma obtained after nasal administration of the aforesaid formulations. The graph shows the appearance of a plasma insulin peak for all formulations between the first fifteen and thirty minutes after administration. The plasma insulin profile is similar for all formulations. Analysis of the area under the curve of the plasma insulin concentration shows that the only statistically significant difference is to be found between the highest dose and the lowest dose of HYAFF-11. It can also be seen that an eightfold increase in the dose of HYAFF-11 only doubles the area under the curve. In conclusion, the results show that this system can be applied to humans where low doses of microspheres can be used to administer insulin.

EXAMPLE 41

Microspheres of different dimensions of HYAFF-11 containing GM1 (10–40 μm) were prepared as described in Examples 29–30.

The ganglioside was administered by intramuscular route to groups of New Zealand rabbits (weighing 2.5 kg) at a concentration of 2 mg/kg.

At the set times, 2.5 ml of blood was withdrawn from the median artery of the ear. Each blood sample was incubated at 37° C. for one hour and then refrigerated overnight at 4° C. The samples were then centrifuged and the upper layer of serum was removed. 2 ml of tetrahydrofurane (THF) were added to 500 μl of serum for the determination of the GM1 content. The sample was stirred and centrifuged and the upper layer was stored. The precipitate was treated twice with 2 μl of THF and 500 μl of phosphate buffer (50 mM) and centrifuged. The upper layers thus obtained were extracted with ethyl ether after separation of the aqueous phase, the organic phase was further extracted with water. The two aqueous phases were then mixed and freeze-dried. The freeze-dried product was redissolved in water and the $GM_1$ content determined by the ELISA test.

Figure 5:
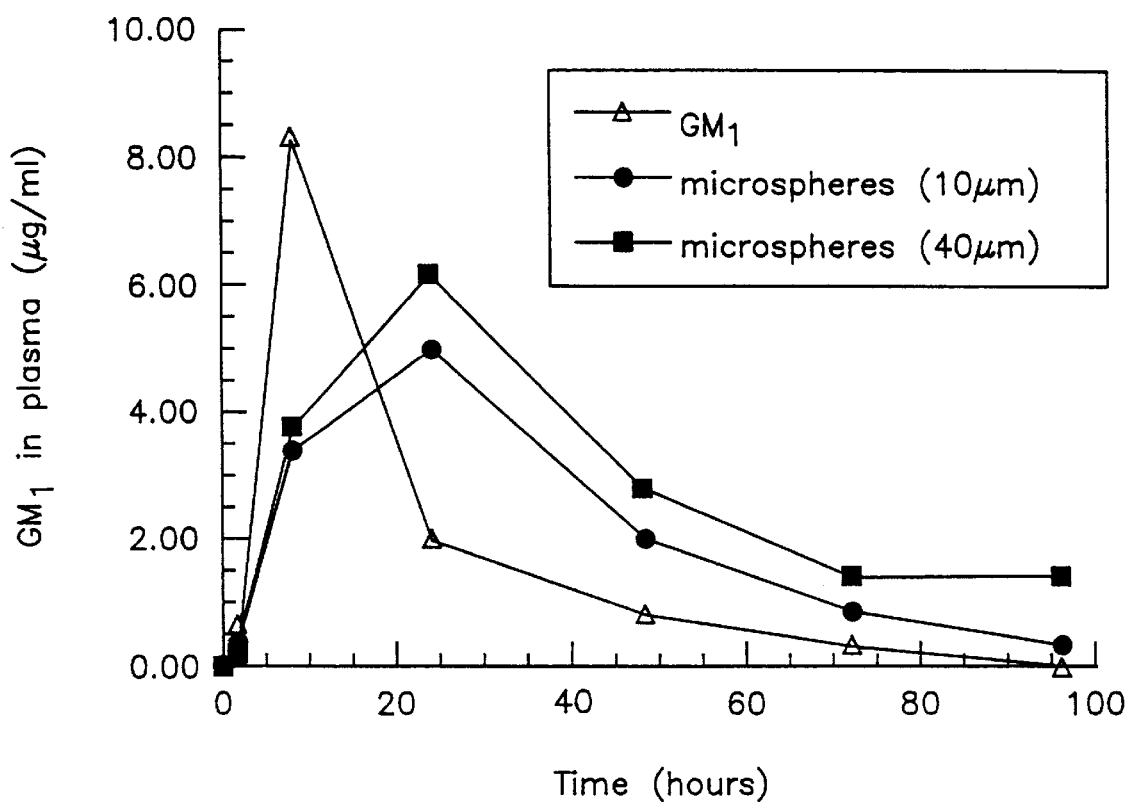
FIG. 5 shows the plasma levels of $GM_1$ after intramuscular administration to rabbits, on its own and with microspheres of different diameters.

The graph in FIG. 5 shows the levels of $GM_1$ in plasma after intramuscular administration.

It can be seen that when the drug is associated with the microspheres, the time needed to reach maximum concentration in the plasma is longer than that required by $GM_1$ administered on its own. Moreover, while plasma levels of $GM_1$ fall rapidly when it is administered on its own, the $GM_1$ lasts longer in plasma when administered with microspheres, because the drug release is slower.

As reported in Table 3, which shows the areas under the curves after $GM_1$ administration in the three different formulations. As can be seen, microspheres with larger diameters (40 μm) guarantee the presence of the drug in the circulation for longer than those with a smaller diameter, probably because the diffusion time of $GM_1$ from the larger microspheres is longer.

TABLE 2

Area under curvce after i.m. administration of $GM_1$ at a concentration of 2 mg/kg (μg/hr/ml)

| Experiment | $GM_1$ | HYAFF-11 (10 μm) | HYAFF-11 (40 μm) |
|---|---|---|---|
| 1st study | 127.74 | 167.06 | 253.4 |
| 2nd study | 134.43 | 158.25 | 223.29 |

EXAMPLE 42

Microspheres containing NGF and NGF+$GM_1$ were prepared with different polymeric matrices, chosen according to the different chemical-physical characteristics of the polymer (Examples 6-8-9-20-21). Three types of the hyaluronic acid derivatives used are reported here as examples: (HYAFF-11; HYAFF-11 p75; HYAFF-7).

Figure 6:
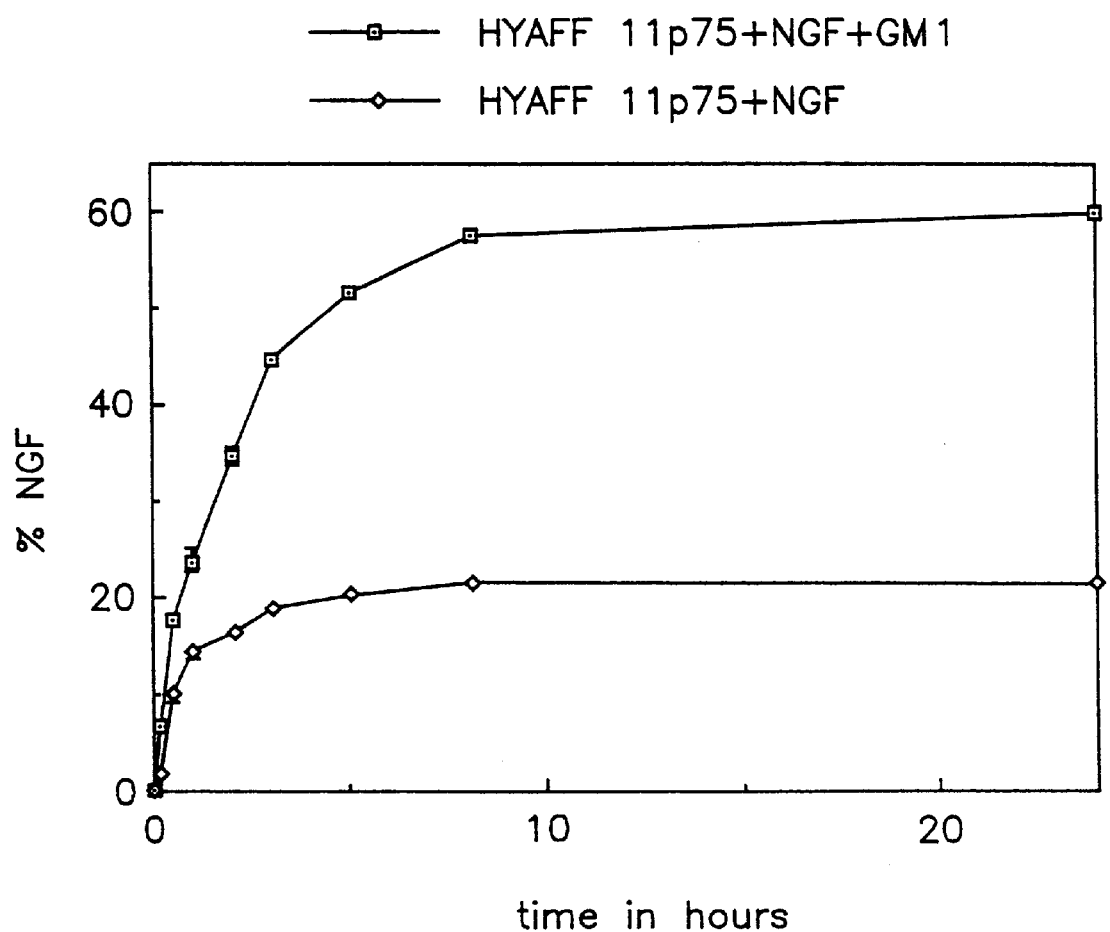
FIG. 6 shows the NGF released from microspheres of HYAFF-11 p75.

To highlight the effect of the different chemical-physical characteristics of the derivatives used in the preparation of the microspheres, the release times of the incorporated products (NGF and GM1) were assessed in vitro. Samples of microspheres were suspended in phosphate buffer 0.1M (pH 7.4) u=0.3 M and kept at 37° C. under constant stirring. Samples were taken at various times and the fractions thus gathered were analysed by HPLC to measure the GM1 present and by an ELISA method to measure NGF. The release of NGF followed a particular pattern in relation to the chemical-physical characteristics of the polymer used to prepare the microspheres and depending on the presence or absence of GM1 in the formulation. In those without GM1, as expected, NGF was released and quantified according to the hydrophilic characteristics of the matrix used. FIG. 6 reports as an example the release of NGF from HYAFF-11 p75 in the presence/absence of GM1. It can be seen that the release of NGF is more abundant and faster in the presence of GM1 than in the samples without ganglioside, for this type of microsphere.

Figure 7:
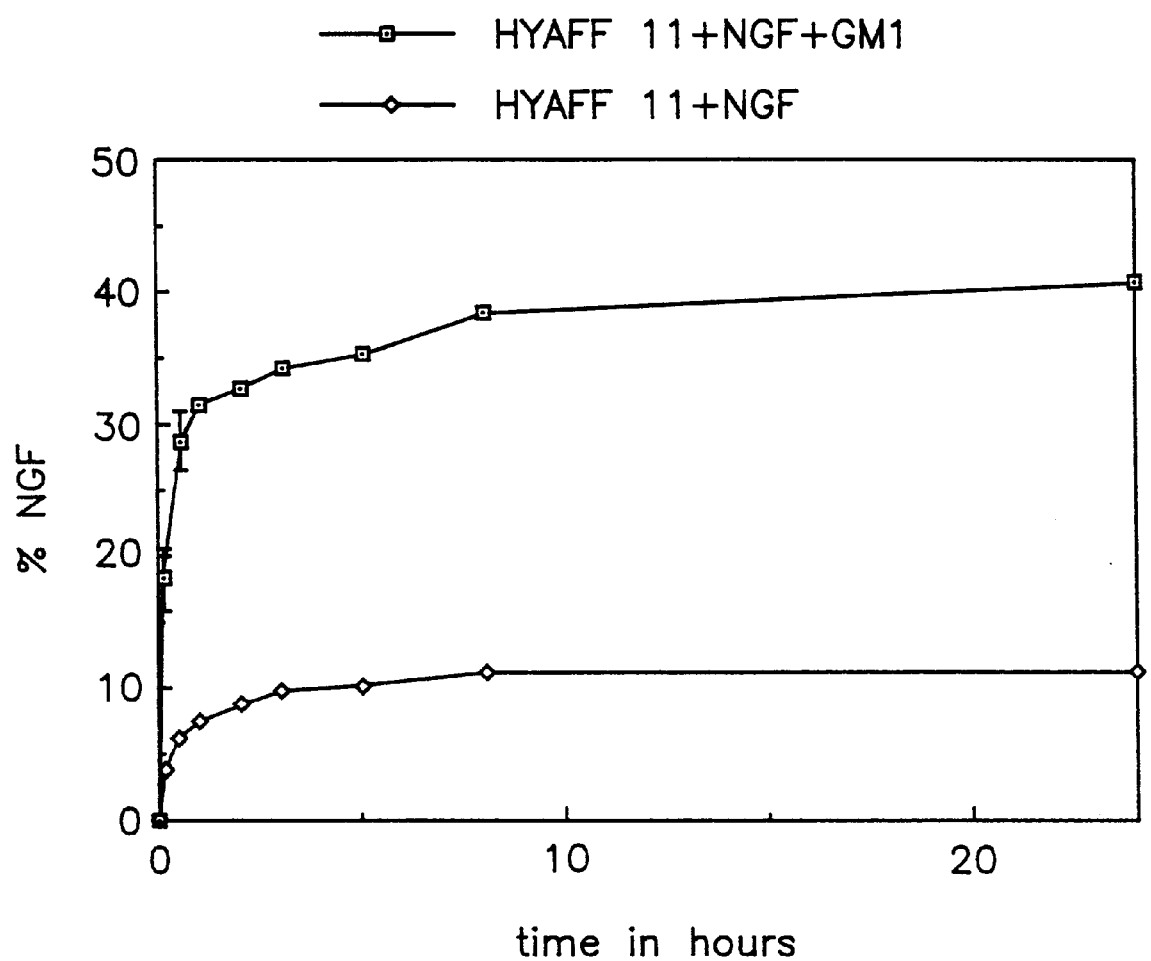
FIG. 7 shows the NGF released from microspheres of HYAFF-11.
Figure 8:
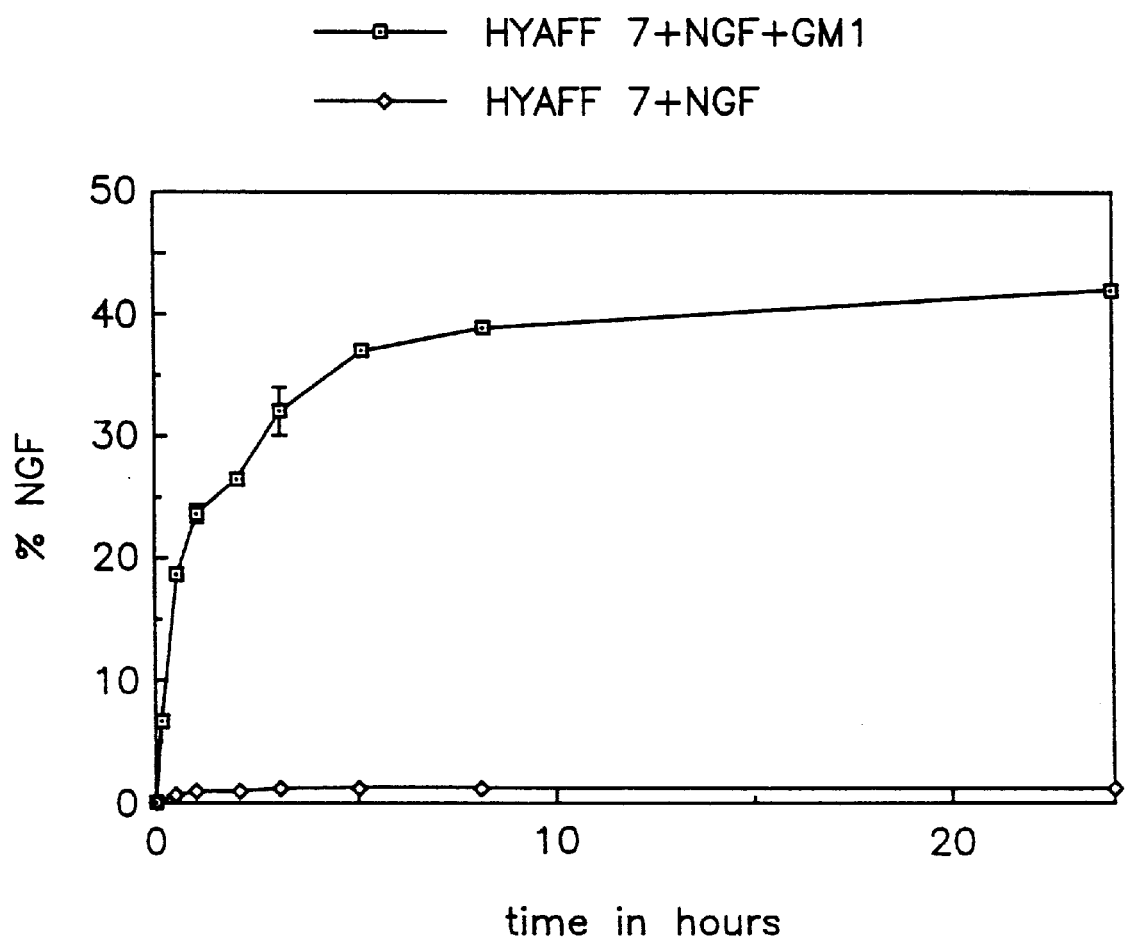
FIG. 8 shows the NGF released from microspheres of HYAFF-7.

In the case of formulations made with totally esterified hyaluronic acid derivatives, it was seen that NGF was released from the polymer matrix in low quantities, showing that there is a strong polymer-polypeptide interaction. But when GM1 was present in the same formulations, it was possible to observe significantly higher levels of NGF in solution (FIGS. 7–8) even though the maximum amount of NGF released was 40% of that incorporated, showing again the strong interaction with the polymer. The invention being thus described, it is clear that these methods can be modified in various ways. Such modifications are not to be considered divergences from the spirit and purpose of the invention, and any modification which would appear evident to an expert in the field come within the scope of the following claims:

We claim:

1. A method for administering a biologically active molecule across the nasal mucosal membrane which comprises administering an effective amount of a smooth surface microsphere which comprises a biologically active molecule and an ester of hyaluronic acid, wherein said biologically active molecule is adhered to said ester of hyaluronic acid, wherein said smooth surface microsphere has a diameter of between 1 μm to 100 μm, and wherein said smooth surface microsphere is formed by a process comprising:
  dissolving said ester of hyaluronic acid and said biologically active molecule in dimethylsulfoxide to produce a mixture;
  adding said mixture to mineral oil with stirring to produce an emulsion;
  adding ethyl acetate to said emulsion to produce a suspension;
  filtering said suspension; and
  recovering smooth surface microspheres thus formed, to said nasal mucosal membrane.

2. The method according to claim 1, wherein said biologically active molecule is insulin.

3. The method according to claim 1, wherein the size of said microsphere is from 1 to 15 microns.

4. A method for administering a biologically active molecule across the nasal mucosal membrane which comprises administering an effective amount of a microsphere which comprises a biologically active molecule and an ester of hyaluronic acid or mixtures of said esters of hyaluronic acids, and wherein said biologically active molecule is surrounded by or adhered to said ester of hyaluronic acid or mixtures thereof, and wherein said microsphere has a diameter of between 1 micron to 100 microns, to said nasal mucosal membrane.

5. The method according to claim 4, wherein the size of said microsphere is from 1 to 15 microns.

6. The method according to claim 4, wherein said biologically active molecule is insulin.

* * * * *